United States Patent
Thallapuranam et al.

(10) Patent No.: US 11,267,855 B2
(45) Date of Patent: Mar. 8, 2022

(54) ENGINEERED FGF1 AND FGF2 COMPOSITIONS AND METHODS OF USE THEREOF

(71) Applicant: THE BOARD OF TRUSTEES OF THE UNIVERSITY OF ARKANSAS, Little Rock, AR (US)

(72) Inventors: Suresh Kumar Thallapuranam, Fayetteville, AR (US); Shilpi Agarwal, Fayetteville, AR (US); Ravi Kumar Gundampati, Fayetteville, AR (US); Srinivas Jayanthi, Fayetteville, AR (US); Tengjiao Wang, Fayetteville, AR (US); Jake Jones, Fayetteville, AR (US); Olivia Kolenc, Fayetteville, AR (US); Ngoc Lam, Fayetteville, AR (US); Isabelle Niyonshuti, Fayetteville, AR (US); Kartik Balachandran, Fayetteville, AR (US); Kyle Quinn, Fayetteville, AR (US); Jingyi Chen, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/356,872

(22) Filed: Mar. 18, 2019

(65) Prior Publication Data
US 2019/0284252 A1   Sep. 19, 2019

Related U.S. Application Data

(60) Provisional application No. 62/644,076, filed on Mar. 16, 2018.

(51) Int. Cl.
  C07K 14/50   (2006.01)
  A61K 9/06    (2006.01)
  A61K 38/00   (2006.01)
  A61K 38/18   (2006.01)

(52) U.S. Cl.
  CPC ........... *C07K 14/501* (2013.01); *A61K 9/06* (2013.01); *C07K 14/503* (2013.01); *A61K 38/00* (2013.01); *A61K 38/1825* (2013.01); *C07K 2319/00* (2013.01)

(58) Field of Classification Search
  None
  See application file for complete search history.

(56) References Cited

U.S. PATENT DOCUMENTS

| | | | |
|---|---|---|---|
| 6,982,170 | B1 | 1/2006 | Maciag |
| 7,396,664 | B2 | 7/2008 | Daly |
| 8,153,770 | B1 | 4/2012 | Blaber |
| 9,657,075 | B2 | 5/2017 | Mohammadi |
| 10,385,113 | B2 | 8/2019 | Thallapuranam |
| 2006/0217310 | A1 | 9/2006 | Chiu |
| 2010/0286042 | A1 | 11/2010 | Imamura |
| 2015/0111821 | A1 | 4/2015 | Suh |
| 2019/0276510 | A1* | 9/2019 | Evans ................. A61P 3/10 |

FOREIGN PATENT DOCUMENTS

| | | |
|---|---|---|
| CN | 103169658 | 6/2013 |
| CN | 103396985 | 11/2013 |
| CN | 104162148 | 11/2014 |
| WO | 1995026737 | 10/1995 |
| WO | 2006073417 | 7/2006 |
| WO | 2009020802 | 2/2009 |
| WO | 2013068776 | 5/2013 |
| WO | 2014084027 | 6/2014 |
| WO | 2014130659 | 8/2014 |
| WO | 2016089945 | 6/2016 |
| WO | 2015121457 | 12/2016 |
| WO | WO 2018/018010 | * 1/2018 |

OTHER PUBLICATIONS

Tassi, E. et al. Enhancement of fibroblast growth factor (FGF) activity by an FGF-binding protein. J Biol Chem 276, 40247-40253 (2001).
Thomas, K. A., et al. (1991). Structural modifications of acidic fibroblast growth factor alter activity, stability, and heparin dependence. Ann N Y Acad Sci, 638, 9-17.
Tsai, E.C., et al. Matrix inclusion within synthetic hydrogel guidance channels improves specific supraspinal and local axonal regeneration after complete spinal cord transection. Biomaterials 27, 519-533 (2006).
Tsai, M. J., et al. "Acidic FGF promotes neurite outgrowth of cortical neurons and improves neuroprotective effect in a cerebral ischemic rat model." Neuroscience 305: 238-47. (2015).
Tunyogi-Csapo, M. et al. Role of fibroblasts and fibroblast-derived growth factors in periprosthetic angiogenesis. J Orthop Res 25, 1378-1388 (2007).
Wang, Y., et al. "Cell-penetrating peptide TAT-mediated delivery of acidic FGF to retina and protection against ischemia-reperfusion injury in rats." J Cell Mol Med 14(7): (2010).
Wong, P., et al. (1995). Analysis of putative heparin-binding domains of fibroblast growth factor-1. Using sitedirected mutagenesis and peptide analogues. J Biol Chem, 270(43), 25805-25811.
Wu, J. C., et al. (2008). "Nerve repair using acidic fibroblast growth factor in human cervical spinal cord injury: a preliminary Phase I clinical study." J Neurosurg Spine 8(3): 208-14.
Xia, X., et al. Engineering a Cysteine-Free Form of Human Fibroblast Growth Factor-1 for "Second Generation" Therapeutic Application. J Pharm Sci, 105(4), 1444-1453. (2016).

(Continued)

*Primary Examiner* — Marianne P Allen
(74) *Attorney, Agent, or Firm* — Quarles & Brady LLP

(57) ABSTRACT

Engineered FGF1 and FGF2 polypeptides, polynucleotides encoding these polypeptides and DNA constructs, vectors and compositions including these engineered polypeptides are provided herein. The engineered FGF1 and FGF2 polypeptides are more stable than their wild-type counterparts and may be more effective at treating a variety of conditions that FGF1 and FGF2 are useful for treating such as wound healing.

8 Claims, 30 Drawing Sheets

Specification includes a Sequence Listing.

(56) References Cited

OTHER PUBLICATIONS

Xia, X., et al. Mutation choice to eliminate buried free cysteines in protein therapeutics. J Pharm Sci. 2015;104:566-576.
Xia, X., et al. "Pharmacokinetic properties of 2nd-generation fibroblast growth factor-1 mutants for therapeutic application." PLoS One 7(11): e48210 (2012).
Xue, L., et al. The cysteine-free fibroblast growth factor 1 mutant induces heparin-independent proliferation of endothelial cells and smooth muscle cells. J Surg Res 92, 255-260 (2000).
Yang, X., et al. "Fibroblast growth factor signaling in the vasculature." Curr Atheroscler Rep 17(6): 509. (2015).
Yeh, B.K. et al. Structural basis for activation of fibroblast growth factor signaling by sucrose octasulfate. Mol Cell Biol 22, 7184-7192 (2002).
Yun, Y. R., et al. Fibroblast growth factors: biology, function, and application for tissue regeneration. J Tissue Eng, 2010, 218142.
Zakrzewska, M., et al. (2004). Design of fully active FGF-1 variants with increased stability. Protein Eng Des Sel, 17(8), 603-611.
Zakrzewska, M., et al. (2005). Highly stable mutants of human fibroblast growth factor-1 exhibit prolonged biological action. J Mol Biol, 352(4), 860-875.
Zakrzewska, M., et al. (2006). Structural requirements of FGF-1 for receptor binding and translocation into cells. Biochemistry, 45(51), 15338-15348.
Zakrzewska, M., et al. FGF-1: from biology through engineering to potential medical applications. Crit Rev Clin Lab Sci 45, 91-135 (2008).
Zhang, J. et al. "Therapeutic uses of FGFs." Seminars in cell & developmental biology. vol. 53. Academic Press, 2016.
Zhao, T., et al. Acidic and basic fibroblast growth factors involved in cardiac angiogenesis following infarction. Int J Cardiol 152, 307-313 (2010).
Zheng, L., et al. "TAT-Mediated Acidic Fibroblast Growth Factor Delivery to the Dermis Improves Wound Healing of Deep Skin Tissue in Rat." PLoS One 10(8): e0135291 (2015).
Ambrosetti, D., et al. (2008). "Fibroblast growth factor signaling uses multiple mechanisms to inhibit Wnt-induced transcription in osteoblasts." Mol Cell Biol 28(15): 4759-71.
Andreopoulos, F.M. et al. Delivery of basic fibroblast growth factor (bFGF) from photoresponsive hydrogel scaffolds. Biomaterials 27, 2468-2476 (2006).
Arunkumar, A.I. et al. Oligomerization of acidic fibroblast growth factor is not a prerequisite for its cell proliferation activity. Protein Sci 11, 1050-1061 (2002).
Arunkumar, A.I. et al. Structure and stability of an acidic fibroblast growth factor from Notophthalmus viridescens. J Biol Chem 277, 46424-46432 (2002).
Asai, J. et al. Topical application of ex vivo expanded endothelial progenitor cells promotes vascularisation and wound healing in diabetic mice. Int Wound J 10, 527-533 (2012).
Assuncao-Silva, R. C., et al. "Hydrogels and Cell Based Therapies in Spinal Cord Injury Regeneration." Stem Cells Int 2015: 948040.
Beenken, A., et al. "Plasticity in interactions of fibroblast growth factor 1 (FGF1) N terminus with FGF receptors underlies promiscuity of FGF1." J Biol Chem 287(5): 3067-78. 2012.
Beenken, A., et al (2009). The FGF family: biology, pathophysiology and therapy. Nat Rev Drug Discov, 8(3), 235-253.
Bernett, M.J., et al. An atomic resolution structure for human fibroblast growth factor 1. Proteins 57, 626-634 (2004).
Blaber, S. I., et al. Accelerated healing in NONcNZO10/LtJ type 2 diabetic mice by FGF-1. Wound Repair Regen, 23 (4), 538-549. 2015.
Brewster, L.P. et al. Construction and characterization of a thrombin-resistant designer FGF-based collagen binding domain angiogen. Biomaterials 29, 327-336 (2008).
Buchtova, M., et al. "Instability restricts signaling of multiple fibroblast growth factors." Cell Mol Life Sci 72(12): 2445-59. 2015.
Burgess, W. H., et al. (1990). Possible dissociation of the heparin-binding and mitogenic activities of heparin-binding (acidic fibroblast) growth factor-1 from its receptor-binding activities by site-directed mutagenesis of a single lysine residue. J Cell Biol, 111(5 Pt 1), 2129-2138.
Cai, S., et al. Injectable glycosaminoglycan hydrogels for controlled release of human basic fibroblast growth factor. Biomaterials 26, 6054-6067 (2005).
Comerota, A. J. et al. Naked plasmid DNA encoding fibroblast growth factor type 1 for the treatment of end-stage unreconstructible lower extremity ischemia: preliminary results of a phase I trial. J. Vasc. Surg. 35,930-936 (2002).
Culajay, J.F., et al. Thermodynamic characterization of mutants of human fibroblast growth factor 1 with an increased physiological half-life. Biochemistry 39, 7153-7158 (2000).
Dubey, VK, et al. Redesigning symmetry-related "mini-core" regions of FGF-1 to increase primary structure symmetry: thermodynamic and functional consequences of structural symmetry. Protein Sci 14, 2315-2323 (2005).
Dubey, VK, et al. Spackling the crack: stabilizing human fibroblast growth factor-1 by targeting the N and C terminus beta-strand interactions. J Mol Biol. 2007;371(1):256-268.
El Agha, E., et al. Therapeutic and pathological roles of fibroblast growth factors in pulmonary diseases. Dev Dyn, 246(4), 235-244. 2017.
Erzurum, V.Z. et al. R136K fibroblast growth factor-1 mutant induces heparin-independent migration of endothelial cells through fibrin glue. J Vasc Surg 37, 1075-1081 (2003).
Hull, M. A., et al. (1997). "Healing with basic fibroblast growth factor is associated with reduced indomethacin induced relapse in a human model of gastric ulceration." Gut 40(2): 204-10.
Hung, K.W. et al. Solution structure of the ligand binding domain of the fibroblast growth factor receptor: role of heparin in the activation of the receptor. Biochemistry 44, 15787-15798 (2005).
Kelpke, S.S., et al. Site-specific delivery of acidic fibroblast growth factor stimulates angiogenic and osteogenic responses in vivo. J Biomed Mater Res A 71, 316-325 (2004).
Khanna, O., et al. "Generation of alginate microspheres for biomedical applications." JoVE (Journal of Visualized Experiments) 66 (2012): e3388.
Klingenberg, O., et al. (1999). Effects of mutations of a phosphorylation site in an exposed loop in acidic fibroblast growth factor. J Biol Chem, 274(25), 18081-18086.
Kobielak, A., et al. "Protease resistant variants of FGF1 with prolonged biological activity." Protein Pept Lett 21 (5): 434-43. 2014.
Li, M., et al. "FGF1 Mediates Overnutrition-Induced Compensatory beta-Cell Differentiation." Diabetes 65(1): 96-109. 2016.
Lin, P. H., et al. Spinal cord implantation with acidic fibroblast growth factor as a treatment for root avulsion in obstetric brachial plexus palsy. J. Chin. Med. Assoc. 68,392-396 (2005).
Lin, W. H., et al. "Fibroblast growth factors stimulate hair growth through beta-catenin and Shh expression in C57BL/6 mice." Biomed Res Int 2015: 730139.
Martin, P. Wound healing—aiming for perfect skin regeneration. Science 276, 75-81 (1997).
Mellin TN, et al. Acidic fibroblast growth factor accelerates dermal wound healing in diabetic mice. J Invest Dermatol. 1995;104:850-855.
Motomura, K. et al. An FGF1:FGF2 chimeric growth factor exhibits universal FGF receptor specificity, enhanced stability and augmented activity useful for epithelial proliferation and radioprotection. Biochim Biophys Acta 1780, 1432-1440 (2008).
Moya, M.L. et al. The effect of FGF-1 loaded alginate microbeads on neovascularization and adipogenesis in a vascular pedicle model of adipose tissue engineering. Biomaterials 31, 2816-2826 (2010).
Nakayama, F., et al. "Post treatment with an FGF chimeric growth factor enhances epithelial cell proliferation to improve recovery from radiation-induced intestinal damage." Int J Radiat Oncol Biol Phys 78(3): 860-7. 2010.
Nguyen T. H., et al. A heparin-mimicking polymer conjugate stabilizes basic fibroblast growth factor. Nature Chemistry, 2013; 5 (3): 221 DOI: 10.1038/nchem.1573.

(56) References Cited

OTHER PUBLICATIONS

Niebuhr, A., et al. Longterm safety of intramuscular gene transfer of non-viral FGF1 for peripheral artery disease. Gene Ther, 19(3), 264-270. 2012.

Nikol, S. et al. Therapeutic angiogenesis with intramuscular NV1FGF improves amputation-free survival in patients with critical limb ischemia. Mol. Ther. 16, 972-978 (2008).

Ornitz, D. M. et al. "Fibroblast growth factor signaling in skeletal development and disease." Genes Dev 29(14): 1463-86. 2015.

Ortega, S., et al. (1991). Conversion of cysteine to serine residues alters the activity, stability, and heparin dependence of acidic fibroblast growth factor. J Biol Chem, 266(9), 5842-5846.

Pang, Y. et al. Local delivery of a collagen-binding FGF-1 chimera to smooth muscle cells in collagen scaffolds for vascular tissue engineering. Biomaterials 31, 878-885 (2010).

Patrie, K. M., et al. (1999). Site-directed mutagenesis and molecular modeling identify a crucial amino acid in specifying the heparin affinity of FGF-1. Biochemistry, 38(29), 9264-9272.

Perry, R. J., et al. "FGF1 and FGF19 reverse diabetes by suppression of the hypothalamic-pituitary-adrenal axis." Nat Commun 6: 6980. 2015.

Schumacher, B., et al. Induction of neoangiogenesis in ischemicmyocardium by human growth factors: first clinical results of a new treatment of coronary heart disease. Circulation 97, 645-650 (1998).

Shireman, P.K., et al. The S130K fibroblast growth factor-1 mutant induces heparin-independent proliferation and is resistant to thrombin degradation in fibrin glue. J Vasc Surg 31, 382-390 (2000).

Shoichet, B.K., et al. A relationship between protein stability and protein function. Proc Natl Acad Sci U S A 92, 452-456 (1995).

Sokic, S. et al. "FGF-1 and proteolytically mediated cleavage site presentation influence three-dimensional fibroblast invasion in biomimetic PEGDA hydrogels." Acta Biomater 8(6): 2213-22. (2012).

Suh, J.M. et al. Endocrinization of FGF1 produces a neomorphic and potent insulin sensitizer. Nature 513, 436-439 (2014).

Szlachcic, A. et al. Structure of a highly stable mutant of human fibroblast growth factor 1. Acta Crystallogr D Biol Crystallogr 65, 67-73 (2009).

Takahashi, M. et al. Fibroblast growth factor-1-induced ERK1/2 signaling reciprocally regulates proliferation and smooth muscle cell differentiation of ligament-derived endothelial progenitor cell-like cells. Int J Mol Med 29, 357-364 (2012).

Fan, Y., et al. "Ectopic expression of human acidic fibroblast growth factor 1 in the medicinal plant, Salvia miltiorrhiza, accelerates the healing of burn wounds." BMC Biotechnol 14: 74. (2014).

\* cited by examiner

Fig. 2

FGF1

```
wt hFGF1 (SEQ ID NO: 1)      1    MFNLPPGNYKKPKLLYCSNGGHFLRILPDGTVDGTRDRSDQHIQLQLSAESVGEVYIKST     60
super hFGF1 (SEQ ID NO: 2)   1    MFNLPPGNYKKPKLLYCSNGGHFLRILPDGTVDGTRDRSD HIQLQL AESVGEVYIKST     60
                                  MFNLPPGNYKKPKLLYCSNGGHFLRILPDGTVDGTRDRSDPHIQLQLLAESVGEVYIKST wt hFGF1 (SEQ ID NO: 1)     61    ETGQYLAMDTDGLLYGSQTPNEECLFLERLEENHYNTYISKKHAEKNWFVGLKKNGSCKR    120
super hFGF1 (SEQ ID NO: 2)  61    ETGQYLAMDTDGLLYGSQTPNEECLFLERLEEN YNTYISKKHAEKNWFVGL KNGSCKR
                                  ETGQYLAMDTDGLLYGSQTPNEECLFLERLEENSYNTYISKKHAEKNWFVGLNKNGSCKR    120 wt hFGF1 (SEQ ID NO: 1)    121    GPRTHYGQKAILFLPLPVSSD    141
super hFGF1 (SEQ ID NO: 2) 121    GP THYGQKAILFLPLPVSSD
                                  GPETHYGQKAILFLPLPVSSD    141
```

FGF2

```
wt hFGF2 (SEQ ID NO: 3)      1    MAAGSITTLPALPEDGGSGAFPPGHFKDPKRLYCKNGGFFLRIHPDGRVDGVREKSDPHI     60
super hFGF2 (SEQ ID NO: 4)   1    MAAGSITTLPALPEDGGSGAFPPGHFKDPKRLYCKNGGFFLRIHPDGRVDGVREKSDPHI
                                  MAAGSITTLPALPEDGGSGAFPPGHFKDPKRLYCKNGGFFLRIHPDGRVDGVREKSDPHI     60 wt hFGF2 (SEQ ID NO: 3)     61    KLQLQAEERGVVSIKGVCANRYLAMKEDGRLLASKCVTDECFFFERLESNNYNTYRSRKY    120
super hFGF2 (SEQ ID NO: 4)  61    KLQL AEERGVVSIKGVCANRYLAMKEDGRLLASKCVTDECFFFERLESN+YNTYRSRKY
                                  KLQLLAEERGVVSIKGVCANRYLAMKEDGRLLASKCVTDECFFFERLESNSYNTYRSRKY    120 wt hFGF2 (SEQ ID NO: 3)    121    TSWYVALKRTGQYKLGSKTGPGQKAILFLPMSAKS    155
super hFGF2 (SEQ ID NO: 4) 121    TSWYVAL RTGQYKLGS+TGPGQKAILFLPMSAKS
                                  TSWYVALNRTGQYKLGSETGPGQKAILFLPMSAKS    155
```

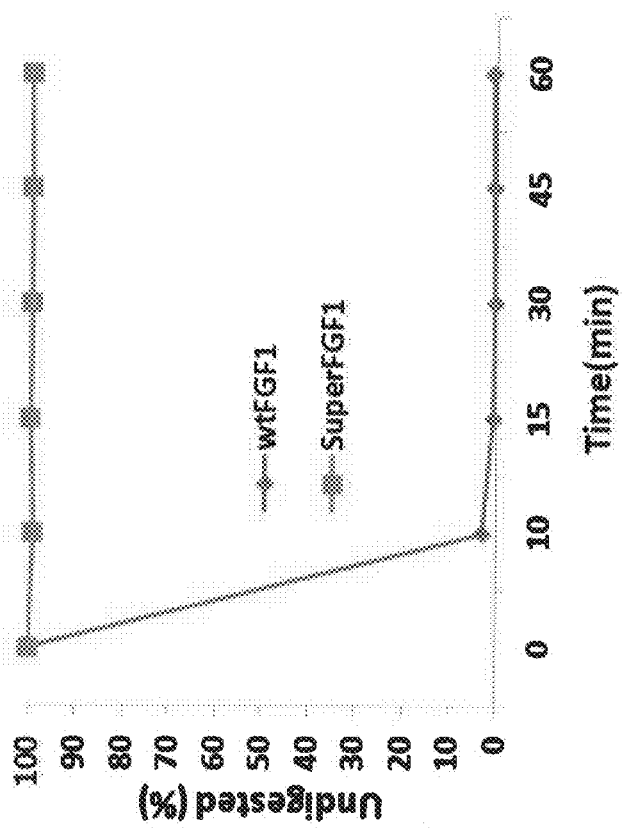
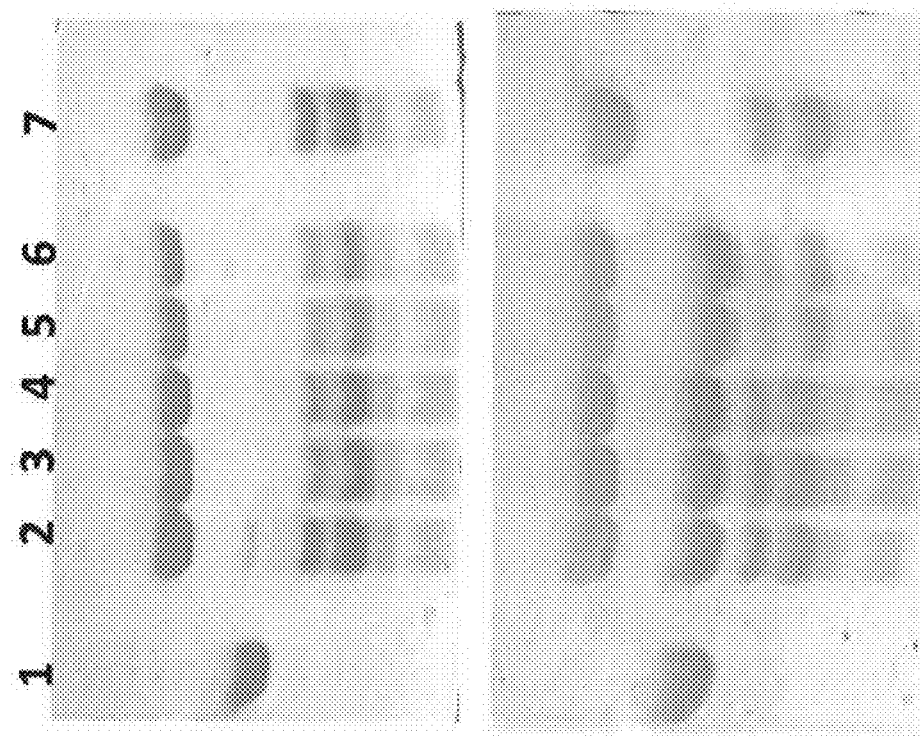

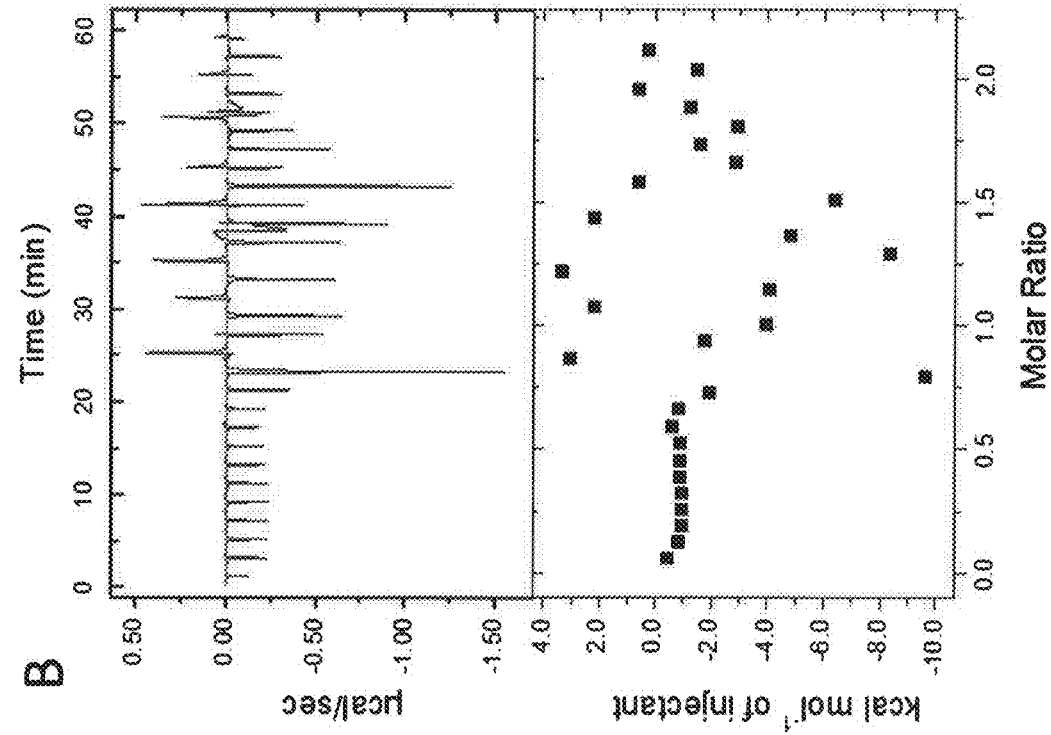
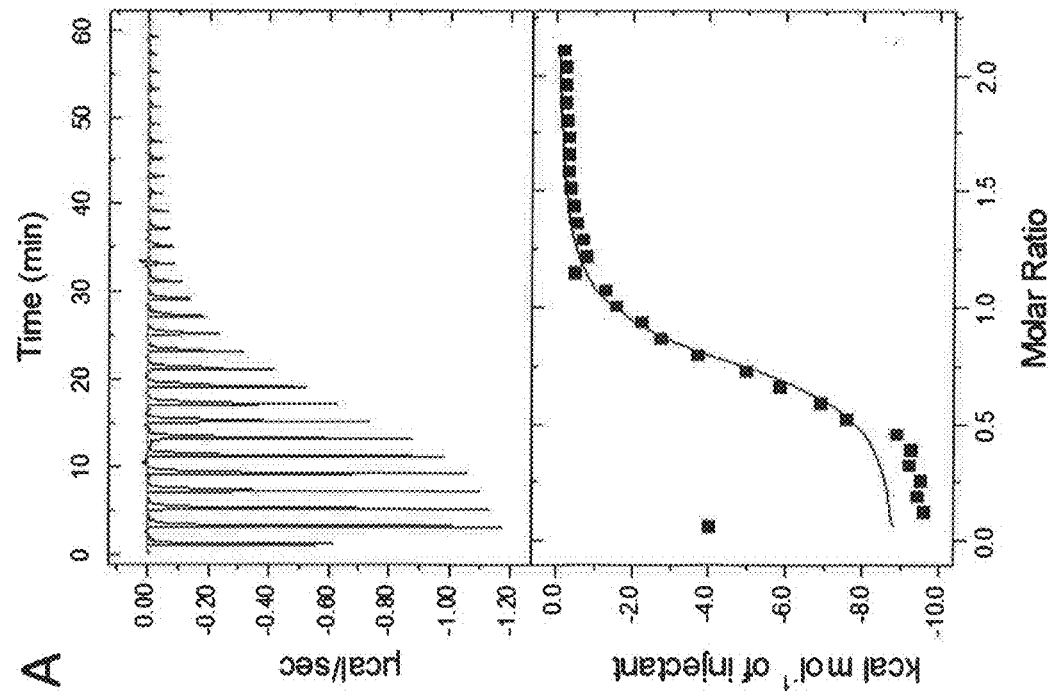
Fig. 13A
Fig. 13B

ENGINEERED FGF1 AND FGF2 COMPOSITIONS AND METHODS OF USE THEREOF

CROSS-REFERENCE TO RELATED APPLICATIONS

This patent application claims the benefit of priority of U.S. Provisional Patent Application No. 62/644,076, filed Mar. 16, 2018, which is incorporated herein by reference in its entirety.

STATEMENT REGARDING FEDERALLY SPONSORED RESEARCH

This invention was made with government support under Grant Numbers P30 GM103450 and P20 RR015569 awarded by the National Institutes of Health, and Grant Number DE-FG02-01ER15161 awarded by the Department of Energy. The government has certain rights in the invention.

FIELD OF INVENTION

The present invention relates to the development of stable mutants of FGF-1 and FGF-2. It relates in particular to polynucleotides, polypeptides, and pharmaceutical compositions including such mutant forms of FGF-1 and FGF-2 as well as methods of treating conditions using such compositions.

SEQUENCE LISTING

This application is being filed electronically via EFS-Web and includes an electronically submitted Sequence Listing in .txt format. The .txt file contains a sequence listing entitled "5965-00118_ST25.txt" created on Mar. 18, 2019 and is 5,822 bytes in size. The Sequence Listing contained in this .txt file is part of the specification and is hereby incorporated by reference herein in its entirety.

INTRODUCTION

Chronic wounds impact ~15% of Medicare beneficiaries. A conservative cost estimate of wound care is ~$31.7 billion. In this context, there is an immediate need for the development of an efficient biotherapeutics for healing wounds. Cytokines, such as, Fibroblast Growth factors (FGFs), have been used in wound care formulations with limited success. FGFs play an important role in various cellular processes like cell proliferation, migration, differentiation and induce processes such as regeneration, morphogenesis and angiogenesis. FGFs exert their effects upon binding to their specific receptors. These molecules are known to bind to heparin to increase the efficiency of mitogenic activity.

FGF-1 is known to play a crucial role in wound healing and other significant clinical conditions. For example, there are reports demonstrating the FGF-1 has significant nerve regeneration and potent angiogenic activity. These events are critical for proper healing after an injury. Hence administration of FGF-1 during an injury can quicken the process of healing and helps in safe recovery from trauma. Although FGF-1 and FGF-2 proteins are promising therapeutics, they have low intrinsic stability and are highly susceptible to proteolytic degradation especially by thrombin which is usually present in abundance at the site of a wound in the fibrin clots. Thus, there is a need in the art for new FGF-based treatments having increased stability against proteolytic degradation, higher biological activity, a prolonged circulation half-life and prolonged shelf stability or stability in common wound treatment media.

SUMMARY

In one aspect, the present invention relates to engineered FGF1 polypeptides. The FGF1 polypeptides may include at least 60%, 70%, 75%, 80%, 85%, 90%, 95%, or 99% sequence identity to SEQ ID NO: 1 and are engineered to include at least 1, 2, 3, or 4 amino acid substitution(s) to SEQ ID NO: 1 selected from the group consisting of Q41P, Q41F, Q41M, Q41Y, Q41W, Q41I, Q41L, Q41V, Q41A, S48L, S48A, S48V, S48P, S48T, S48M, S48L, S48I,S48F, S48Y, S48W, H94S, H94T, H94K, H94R, H94Y, K113N, K113Q, K113S, K113T, K113R, and K113Y, or may include functional fragments of such FGF1 polypeptides. Optionally, the FGF1 polypeptides may further include a R123E amino acid substitution to SEQ ID NO: 1.

In another aspect, the present invention relates to engineered FGF2 polypeptides. The FGF2 polypeptides may include at least 60%, 70%, 75%, 80%, 85%, 90%, 95%, or 99% sequence identity to SEQ ID NO: 3 and are engineered to include at least 1, 2, or 3 amino acid substitution(s) to SEQ ID NO: 3 selected from the group consisting of Q65L, Q65A, Q65P, Q65V, Q65I, Q65M, Q65F, Q65W, Q65Y, N111S, N111Q, N111T, N111Y, K128N, K128Q, K128H, K128R, K128E, K128D, and K128P, or may include functional fragments of such FGF2 polypeptides. Optionally, the FGF2 polypeptides may further include a K138E amino acid substitution to SEQ ID NO: 3.

In another aspect of the present invention, fusion proteins are provided. The fusion proteins may include any one of the FGF1 or FGF2 polypeptides disclosed herein and a membrane permeable peptide.

In a further aspect, polynucleotides encoding any of the FGF1 or FGF2 polypeptides disclosed herein are also provided.

In another aspect of the present invention, DNA constructs are provided. The DNA constructs provided herein may include a promoter operably linked to any one of the polynucleotides described herein.

In yet another aspect, vectors including any of the DNA constructs or polynucleotides described herein are provided.

In a further aspect, pharmaceutical compositions including any of the FGF1 or FGF2 polypeptides, polynucleotides, DNA constructs, or vectors described herein are provided. The pharmaceutical compositions may include a pharmaceutical carrier, excipient, or diluent (i.e., agents).

In a further aspect, hydrogels including any of the FGF1 or FGF2 polypeptides, polynucleotides, DNA constructs, or vectors described herein are provided.

In a still further aspect, methods of treating a condition are also provided. The methods may include administering any of FGF1 or FGF2 polypeptides, polynucleotides, DNA constructs, vectors, pharmaceutical compositions, or hydrogels described herein to a subject in an amount effective to treat the condition. The condition may include a wound (chronic and acute), Type 1 diabetes, Type 2 diabetes, obesity, internal injuries, a cardiovascular disorder, a cosmetic condition (i.e. whitening, wrinkling), critical limb ischemia, a nerve injury, a burn, hair loss (whether genetic or not, i.e. alopecia), a retinal disorder (i.e., retinopathy disorders), a muscular disorder, an arterial disease, an age related disorder, organ or tissue damage (whether or not from chemotherapy or radiation therapy), osteoporosis, a digestive tract ulcer (i.e., gastric ulcer), ulcerative colitis, a scar, an energy homeostasis disorder such as obesity, dyslipidemia, diabetes, insulin resistance, hyperglycemia or the metabolic syndrome, osteoarthritis, and acute renal failure.

BRIEF DESCRIPTION OF THE DRAWINGS

FIG. 2 shows a pairwise alignment of wtFGF1 (SEQ ID NO: 1) against shFGF1 (SEQ ID NO: 2) mutant and wtFGF2 (SEQ ID NO: 3) and shFGF2 (SEQ ID NO: 4).

FIG. 6A shows SDS-PAGE showing the limited trypsin digestion of wt-hFGF1 (Upper) and super hFGF1 (lower) respectively. Lanes 1—0 min, 2—10 min, 3—15 min, 4—30 min, 5—45 min, 6—60 min and 7—pure trypsin. FIG. 6B—densitometric data obtained from SDS-PAGE gels was plotted with Time (min) on X-axis and % Undigested on Y-axis.

FIGS. 13A-13B show isothermograms of wt-hFGF1 (FIG. 13A) and super hFGF1 (FIG. 13B) titrated against heparin. Upper panel represents the heat evolved per injection. Lower panel shows the data fit to the one-set of sites binding model using Origin™ software.

FIG. 16A shows the cell proliferation assay of wt-hFGF1 and super hFGF1 incubated in culture medium. FIG. 16B shows the SDS-PAGE of the samples of wt-hFGF1 and super hFGF1 incubated in the culture medium. Lanes 1 & 5 immediately after addition of medium, 2 & 6—no medium, 3 & 7—medium with no cells for 24 hrs, 4 & 8—incubated with cells in medium for 24 hrs.

DETAILED DESCRIPTION

Figure 1A:
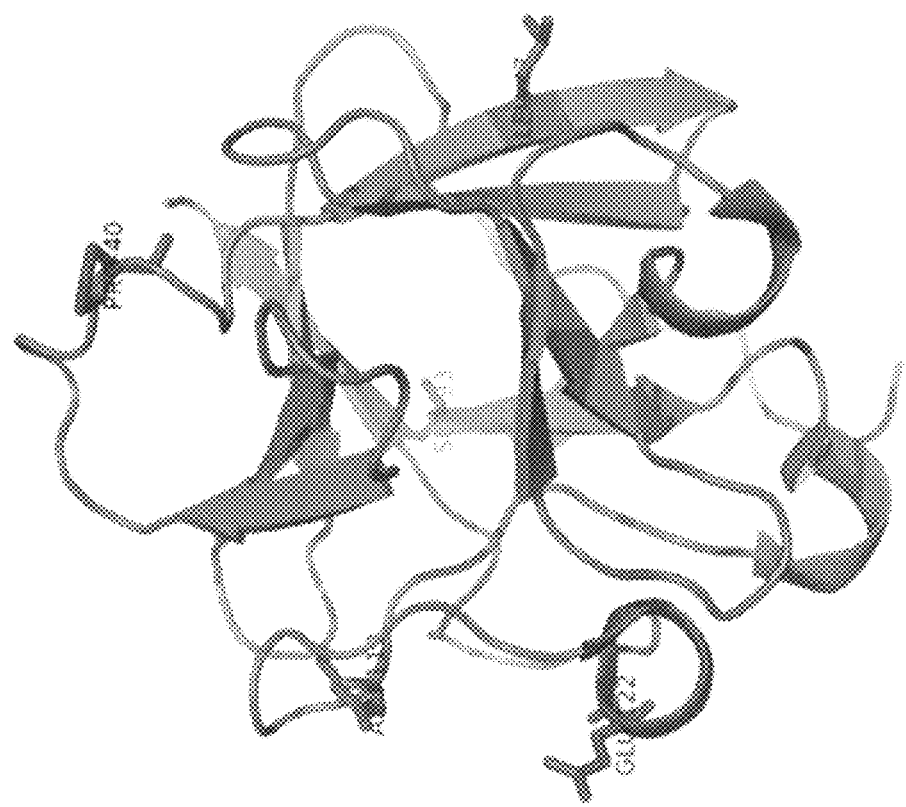
FIGS. 1A-1B show 3D cartoon representations of hFGF1 protein showing the comparison the amino acids between the (FIG. 1A) wt (SEQ ID NO: 1) and (FIG. 1B) super hFGF1 (SEQ ID NO: 2).

The present invention pertains to the development of hyper-stable variants of human FGF1 and FGF2 ("hFGF1" and "hFGF2," respectively) that are not only resistant to thrombin but also exhibit heparin-independent mitogenic/wound healing activity. Due to extraordinary physical and bioactivity of these engineered variants, the present inventors have named an engineered human FGF1 variant (Q41P, S48L, H94S, K113N, and R123E) variant "super human acidic fibroblast growth factor 1 (shFGF1)" and an engineered human FGF2 variant (Q65L, N111S, K128N, and K138E) "super human acidic fibroblast growth factor 2 (shFGF2)." In the nonlimiting Examples, the present inventors demonstrate that super hFGF1 (SEQ ID NO: 2) is a very stable hFGF1 variant. It shows no signs of degradation even when stored at room temperature (25° C.) for over 3 months. ShFGF1 denatures only at temperatures higher than 80° C. ShFGF1 exhibits a wider range of pH stability (4.0-10.0) than wild type hFGF1 (wt-hFGF1; SEQ ID NO: 1). ShFGF1 shows no binding affinity to heparin but its mitogenic activity is higher than that of wt-FGF1. Furthermore, the present inventors postulate that the corresponding amino acid substitutions may be applied to hFGF2 (SEQ ID NO: 3) to create a shFGF2 variant (SEQ ID NO: 4), which will be more stable than the wt human FGF2 protein. The hyper-stability, resistance to thrombin action, and enhanced heparin-independent bioactivity renders shFGF1, shFGF2, and the additional variants disclosed herein as promising biotherapeutics for treating conditions including, without limitation, wounds, osteoporosis, diabetes, hyperglycemia, and insulin resistance.

In one aspect, the present invention relates to engineered FGF1 polypeptides. The FGF1 polypeptides may include at least 60%, 70%, 75%, 80%, 85%, 90%, 95%, or 99% sequence identity to SEQ ID NO: 1 and are engineered to include at least 1, 2, 3, or 4 amino acid substitution(s) to SEQ ID NO: 1 to amino acid residues Q41, S48, H94, or K113 or any combination thereof. The FGF1 polypeptides may include at least 60%, 70%, 75%, 80%, 85%, 90%, 95%, or 99% sequence identity to SEQ ID NO: 1 and are engineered to include at least 1, 2, 3, or 4 amino acid substitution(s) to SEQ ID NO: 1 selected from the group consisting of Q41P, Q41F, Q41M, Q41Y, Q41W, Q41I, Q41L, Q41V, Q41A, S48L, S48A, S48V, S48P, S48T, S48M, S48L, S48I, S48F, S48Y, S48W, H94S, H94T, H94K, H94R, H94Y, K113N, K113Q, K113S, K113T, K113R, and K113Y; or may include functional fragments of such FGF1 polypeptides. In some embodiments, the at least 1, 2, 3, or 4 amino acid substitution(s) to SEQ ID NO: 1 are selected from the group consisting of Q41P, S48L, H94S, K113N and any combination thereof including 1, 2, 3, or all four mutations. Optionally, the FGF1 polypeptides may further include a R123E or R123D amino acid substitution to SEQ ID NO: 1. Suitably, the additional amino acid substitution to SEQ ID NO: 1 is R123E.

In some embodiments, the FGF1 polypeptides may include at least 60%, 70%, 75%, 80%, 85%, 90%, 95%, 99%, or 100% sequence identity to SEQ ID NO: 2 and include amino acid residues 41, 48, 94, 113, and 123 of SEQ ID NO: 2, or may include functional fragments of such FGF1 polypeptides. In some embodiments, the FGF1 polypeptides may include SEQ ID NO: 2.

In another aspect, the present invention relates to engineered FGF2 polypeptides. The FGF2 polypeptides may include at least 60%, 70%, 75%, 80%, 85%, 90%, 95%, or 99% sequence identity to SEQ ID NO: 3 and are engineered to include at least 1, 2, or 3 amino acid substitution(s) to SEQ ID NO: 3 to amino acid residues Q65, N111, K128 or any combination thereof. The FGF2 polypeptides may also include at least 60%, 70%, 75%, 80%, 85%, 90%, 95%, or 99% sequence identity to SEQ ID NO: 3 and are engineered to include at least 1, 2, or 3 amino acid substitution(s) to SEQ ID NO: 3 selected from the group consisting of Q65L, Q65A, Q65P, Q65V, Q65I, Q65M, Q65F, Q65W, Q65Y, N111S, N111Q, N111T, N111Y, K128N, K128Q, K128H, K128R, K128E, K128D, and K128P; or may include functional fragments of such FGF2 polypeptides. In some embodiments, the at least 1, 2, or 3 amino acid substitution(s) to SEQ ID NO: 3 are selected from the group consisting of Q65L, N111S, K128N and combinations thereof. Optionally, the FGF2 polypeptides may further include a K138E or K138D amino acid substitution to SEQ ID NO: 3. Suitably, the additional amino acid substitution to SEQ ID NO: 3 is K138E.

In some embodiments, the FGF2 polypeptides may include at least 60%, 70%, 75%, 80%, 85%, 90%, 95%, 99%, or 100% sequence identity to SEQ ID NO: 4 and include amino acid residues 65, 111, 128, and 138 of SEQ ID NO: 4, or may include functional fragments of such FGF2 polypeptides. In some embodiments, the FGF2 polypeptide may include SEQ ID NO: 4.

As used herein, the terms "protein" or "polypeptide" or "peptide" may be used interchangeably to refer to a polymer of amino acids. A "polypeptide" as contemplated herein typically comprises a polymer of naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation, lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, enzymatic addition such as polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine) are also contemplated.

The FGF1 and FGF2 polypeptides provided herein are engineered polypeptides representing substitution mutants of the wild-type polypeptide. The FGF1 and FGF2 polypeptides disclosed herein may include "mutant" FGF polypeptides and variants thereof. As used herein the term "wild-type" is a term of the art understood by skilled persons and means the typical form of an organism, strain, gene or characteristic as it occurs in nature as distinguished from mutant or variant forms. As used herein, a "variant" refers to a polypeptide molecule having an amino acid sequence that differs from a reference protein or polypeptide molecule. A variant may have one or more insertions, deletions, or substitutions of an amino acid residue relative to a reference molecule. A variant may include a fragment of a reference molecule. For example, a FGF1 polypeptide variant molecule may have one or more insertions, deletions, or substitution of at least one amino acid residue relative to the mutant FGF1 polypeptides described herein.

The amino acid sequence of the "wild-type" FGF1 protein from humans is presented as SEQ ID NO: 1. See FIG. 2. The amino acid sequence of the "wild-type" FGF2 protein from humans is presented as SEQ ID NO: 3. See FIG. 2. Amino acid sequences for engineered mutant FGF1 and FGF2 polypeptides disclosed herein are provided as SEQ ID NO: 2 (FGF1-Q41P, S48L, H94S, K113N, R123E) and SEQ ID NO: 4 (FGF2-Q65L, N111S, K128N, K138E). See FIG. 2. These sequences may be used as reference sequences.

The FGF1 and FGF2 polypeptides provided herein may be full-length polypeptides (i.e., SEQ ID NOS: 1-4) or may be functional fragments of the full-length FGF polypeptide. As used herein, a "fragment" or "functional fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 155 contiguous amino acid residues of a reference polypeptide, respectively. In some embodiments, a fragment may comprise at least 5, 10, 15, 20, 25, 30, 40, 50, 60, 70, 80, 90, 100, or 150 contiguous amino acid residues of a reference polypeptide. Fragments may be preferentially selected from certain regions of a molecule. The term "at least a fragment" encompasses the full length polypeptide. A fragment of a FGF1 or FGF2 polypeptide may comprise or consist essentially of a contiguous portion of an amino acid sequence of the full-length FGF polypeptide (SEQ ID NOS: 1-4). A fragment may include an N-terminal truncation, a C-terminal truncation, or both truncations relative to the full-length FGF1 or FGF2 polypeptide.

Preferably, a fragment of a FGF1 polypeptide includes amino acid residues 41, 48, 94, 113, and 123 of SEQ ID NO: 2. Preferably, a fragment of a FGF2 polypeptide includes amino acid residues 65, 111, 128, and 138 of SEQ ID NO: 4. Suitable fragments include or consist of amino acid residues 112-128, 106-134, 100-140, 50-140, 25-140, 10-140, 2-140 or any range therein of SEQ ID NOs: 1-2, or amino acid residues 128-144, 120-150, 110-155, 100-155, 80-155, 60-155, 40-155, 20-155, 10-155, 2-155 or any range therein of SEQ ID NOs: 3-4.

FGF1 and/or FGF2 polypeptides may be useful for a variety of reasons. For example, FGF and/or FGF2 polypeptides which contain the substitutions noted above can be used inter alia for raising antibodies. Such polypeptides are typically less than full-length proteins. Preferably such residues are at least 6, 7, 8, 9, 10, 11, 12, 13, 14, 15, 17, 19, 21, 23, 25, 30, 40, 50 or more residues in length. As an example, if the polypeptide is 6 residues in length, than it can comprise residues including the substitution site. Sufficient residues are desired to form a good immunogen or blocking antigen for use in assays. It may be desirable to conjugate or genetically fuse additional sequences to the polypeptide, for example, to boost immunogenicity, to enhance purification, to facilitate production or expression, or to facilitate detection. Any sequences as are convenient may be used for these or other purposes. The size of these additional sequences may vary greatly, but typically will be at least 2, 4, 6, or 8 amino acid residues in length. Suitably the additional sequences will be less than 100, 90, 80, 70, 60, 50, 40, 30, 20 or 10 amino acids in length.

A "deletion" in a FGF1 and/or FGF2 polypeptide refers to a change in the amino acid sequence which results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in a FGF1 and/or FGF2 polypeptide refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of a FGF1 and/or FGF2 polypeptide may have N-terminal insertions, C-terminal insertions, internal insertions, or any combination of N-terminal insertions, C-terminal insertions, and internal insertions.

Regarding polypeptides, the phrases "percent identity," "% identity," and "% sequence identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

As described herein, variants of the engineered mutant FGF1 polypeptides disclosed herein may have 100%, 99%, 98%, 97%, 96%, 95%, 94%, 93%, 92%, 91%, 90%, 80%, 70%, 60%, or 50% amino acid sequence identity relative to a reference molecule (e.g., relative to the FGF1 full-length mutant polypeptides (i.e., SEQ ID NO: 2)). In some embodiments, variants of the engineered mutant FGF1 polypeptides disclosed herein may have 100%, 99%, 98%, 97%, 96%, 95%, 94%, 93%, 92%, 91%, 90%, 80%, 70%, 60%, or 50% amino acid sequence identity relative to a reference molecule (e.g., relative to the FGF1 full-length mutant polypeptides (i.e., SEQ ID NO: 2) and include amino acid residues 41, 48, 94, 113, and 123 of SEQ ID NO: 2. Suitably the variants include the FGF1 substitution mutations identified herein.

As described herein, variants of the engineered mutant FGF2 polypeptides disclosed herein may have 100%, 99%, 98%, 97%, 96%, 95%, 94%, 93%, 92%, 91%, 90%, 80%, 70%, 60%, or 50% amino acid sequence identity relative to a reference molecule (e.g., relative to the FGF2 full-length mutant polypeptides (i.e., SEQ ID NO: 4)). In some embodiments, variants of the engineered mutant FGF2 polypeptides disclosed herein may have 100%, 99%, 98%, 97%, 96%, 95%, 94%, 93%, 92%, 91%, 90%, 80%, 70%, 60%, or 50% amino acid sequence identity relative to a reference molecule (e.g., relative to the FGF2 full-length mutant polypeptides (i.e., SEQ ID NO: 4) and include amino acid residues 65, 111, 128, and 138 of SEQ ID NO: 4. Suitably the variants include the FGF2 substitution mutations identified herein.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

The amino acid sequences of the FGF1 and FGF2 polypeptide variants as contemplated herein may include conservative amino acid substitutions relative to a reference amino acid sequence. For example, a variant or derivative FGF1 or FGF2 polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The amino acid sequences of the FGF1 and FGF2 polypeptide variants as contemplated herein may include may include modifications made apparent by a sequence alignment of the FGF1 and FGF2 polypeptides disclosed herein and other FGF polypeptides. A person of ordinary skill in the art could easily align the FGF1 and FGF2 polypeptides disclosed herein with FGF polypeptides from, for example, other species to determine what additional variants (i.e. substitutions, insertions, deletions, etc.) could be made to the engineered FGF polypeptides. For example, a person of ordinary skill in the art would appreciate that modifications in a reference FGF1 or FGF2 polypeptide could be based on alternative amino acid residues that occur at the corresponding position in other homologous FGF polypeptides from other species.

The disclosed FGF1 and FGF2 polypeptides, mutants, or variants described herein may have one or more functional or biological activities exhibited by a reference polypeptide (e.g., one or more functional or biological activities exhibited by wild-type FGF1 polypeptide (SEQ ID NO: 1) or wild-type FGF2 polypeptide (SEQ ID NO: 3)). For example, the disclosed FGF1 and FGF2 polypeptides, mutants, variants, or derivatives thereof may have increased mitogenic activity or increased stability to protease degradation.

In another aspect of the present invention, fusion proteins are provided. The fusion proteins may include any one of the FGF1 or FGF2 polypeptides disclosed herein and a membrane permeable peptide. The membrane permeable peptide may be any polypeptide having less than 50, 40, 30, or 20 amino acids that can penetrate cell membranes and deliver conjugated FGF polypeptides into cells. Suitable membrane permeable peptide may include, without limitation, a cell-penetrating polypeptide (CPP), TAT, Pep-1, Penetratin, SynB1, SynB3, PTD-4, PTD-5, Transportan, MAP, SBP, FBP, Polyarginines, or Polylysines. The FGF polypeptides provided herein may also be linked to another protein for targeting the FGF to a site or tissue type within the body. For example a fibrin, thrombin, fibronectin or collagen binding protein or polypeptide.

Polynucleotides encoding any of the FGF1 or FGF2 polypeptides disclosed herein are also provided. The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

Isolated polynucleotides homologous to the polynucleotides described herein are also provided. Those of skill in the art also understand the degeneracy of the genetic code and that a variety of polynucleotides can encode the same polypeptide. In some embodiments, the polynucleotides may be codon-optimized for expression in a particular cell such as, without limitation, a mammalian cell or a prokaryotic cell. While particular nucleotide sequences which are found in humans are disclosed herein any nucleotide sequences may be used which encode a desired form of the substituted polypeptides described herein. Thus non-naturally occurring sequences may be used. These may be desirable, for example, to enhance expression in heterologous expression systems of polypeptides or proteins. Computer programs for generating degenerate coding sequences are available and can be used for this purpose as well as other means.

The isolated polynucleotides or polypeptides provided herein may be prepared by methods available to those of skill in the art. Isolated indicates that the polynucleotides or proteins are not in their naturally occurring state. Such preparations may be cell-free preparations. The polynucleotide or polypeptides may be extracted from the cells by breaking the cell membrane and optionally removing non-desired components. The polypeptides may be made as secreted polypeptides and further isolated using means known to those of skill in the art. Alternatively, desired proteins or nucleic acids can be purified using sequence-specific reagents, including but not limited to oligonucleotide probes, primers, and antibodies. Techniques for isolating cell-free preparations are well known in the art, and any that are convenient can be used. The term "substantially isolated or purified" refers to polypeptides or polynucleotides that are removed from their natural environment, and are at least 60% free, preferably at least 75% free, and more preferably at least 90% free, even more preferably at least 95% free from other components with which they are naturally associated.

In another aspect of the present invention, DNA constructs are provided. As used herein, the term "DNA construct" refers to recombinant DNA polynucleotides which may be single-stranded or double-stranded and may represent the sense or the antisense strand or both. Recombinant polynucleotides are polynucleotides formed by laboratory methods that include polynucleotide sequences derived from at least two different natural sources or they may be synthetic. Constructs thus may include new modifications to endogenous genes introduced by, for example, genome editing technologies. Constructs may also include recombinant polynucleotides created using, for example, recombinant DNA methodologies.

The DNA constructs provided herein may be prepared by methods available to those of skill in the art. Notably each of the DNA constructs claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The DNA constructs provided herein may include a promoter operably linked to any one of the polynucleotides described herein. The promoter may be a heterologous promoter or an endogenous promoter associated with the FGF1 or FGF2 polypeptide.

As used herein, the terms "heterologous promoter," "promoter," "promoter region," or "promoter sequence" refer generally to transcriptional regulatory regions of a gene, which may be found at the 5' or 3' side of the FGF1 or FGF2 polynucleotides described herein, or within the coding region of the FGF1 or FGF2 polynucleotides, or within introns in the FGF1 or FGF2 polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the disclosed FGF1 or FGF2 polynucleotides are operably connected to the promoter. As used herein, a polynucleotide is "operably connected" or "operably linked" when it is placed into a functional relationship with a second polynucleotide sequence. For instance, a promoter is operably linked to an FGF1 or FGF2 polynucleotide if the promoter is connected to the FGF1 or FGF2 polynucleotide such that it may effect transcription of the FGF1 or FGF2 polynucleotides. In various embodiments, the FGF1 or FGF2 polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be an animal, plant, bacterial, or fungal promoter. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-1α promoter or ubiquitin promoter. Other promoters include the T3, T7 and SP6 promoter sequences, which are often used for in vitro transcription of RNA. Those of skill in the art are familiar with a wide variety of additional promoters for use in various cell types. In some embodiments, the heterologous promoter includes a mammalian promoter, either endogenous to the animal host or heterologous.

Vectors, including any of the DNA constructs or polynucleotides described herein, are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons. Vectors may carry genetic elements, such as those that confer resistance to certain drugs or chemicals.

Pharmaceutical compositions including any of the FGF1 or FGF2 polypeptides, polynucleotides, DNA constructs, or vectors described herein are provided. The pharmaceutical compositions may include a pharmaceutical carrier, excipient, or diluent (i.e., agents), which are nontoxic to the cell or mammal being exposed thereto at the dosages and concentrations employed. Often a pharmaceutical agent is in an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant.

Hydrogels including any of the FGF1 or FGF2 polypeptides, polynucleotides, DNA constructs, or vectors described herein are provided. Suitably, the hydrogels include any one of the FGF1 or FGF2 polypeptides disclosed herein. As used herein, a "hydrogel" refers to a gel in which the liquid component is water.

Methods of treating a condition are also provided. The methods may include administering any of FGF1 or FGF2 polypeptides, polynucleotides, DNA constructs, vectors, pharmaceutical compositions, or hydrogels described herein to a subject in an amount effective to treat the condition. The condition may include a wound (chronic and acute), Type 1 diabetes, Type 2 diabetes, obesity, internal injuries, a cardiovascular disorder, a cosmetic condition (i.e. whitening, wrinkling), critical limb ischemia, a nerve injury, a burn, hair loss (whether genetic or not, i.e. alopecia), a retinal disorder (i.e., retinopathy disorders), a muscular disorder, an arterial disease, an age related disorder, organ or tissue damage (whether or not from chemotherapy or radiation therapy), osteoporosis, a digestive tract ulcer (i.e., gastric ulcer), ulcerative colitis, a scar, an energy homeostasis disorder such as obesity, dyslipidemia, diabetes, insulin resistance, hyperglycemia or the metabolic syndrome, osteoarthritis, and acute renal failure.

The subject may be any mammal, suitably a human, domesticated animal such as a dog, cat, horse, cow, pig, or a mouse or rat. Treating the condition or treatment includes but is not limited to ameliorating at least one symptom of the condition, reducing or slowing further progression of the condition, reducing or slowing the spread of the condition to unaffected areas. Treating a subject refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

An effective amount or a therapeutically effective amount as used herein means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The compositions (i.e. FGF1 or FGF2 polypeptides, polynucleotides, DNA constructs, vectors, pharmaceutical compositions, or hydrogels) described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, intralesional, intra-tumoral, intradermal, or transmucosal absorption. Thus the compositions may be formulated as an ingestible, injectable, topical or suppository formulation. The compositions may also be delivered with in a liposomal or time-release vehicle. The methods may also include an electrical stimulation or electroporation step to aid entry of the polypeptides, polynucleotides, or pharmaceutical compositions into the intracellular space. Administration of the compositions to a subject in accordance with the invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol.

The maximal dosage for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will improve wound healing or other condition being treated by at least 10%, 20%, 30%, 40%, 50%, 60%, 70%, 80%, 90%, 100% or more as compared to no treatment.

The effective dosage amounts described herein refer to total amounts administered, that is, if more than one composition is administered, the effective dosage amounts correspond to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

The FGF1 or FGF2 polypeptides, polynucleotides, DNA constructs, vectors, pharmaceutical compositions, or hydrogels described herein may be administered one time or more than one time to the subject to effectively improve wound healing or other condition being treated. Suitable dosage ranges are of the order of several hundred micrograms effective ingredient with a range from about 0.01 to 10 mg/kg/day, preferably in the range from about 0.1 to 1 mg/kg/day. Precise amounts of effective ingredient required to be administered depend on the judgment of the practitioner and may be peculiar to each subject. It will be apparent to those of skill in the art that the therapeutically effective amount of the polypeptides, polynucleotides, and pharmaceutical compositions described herein will depend, inter alia, upon the administration schedule, the unit dose of antigen administered, whether the composition is administered in combination with other therapeutic agents, the status and health of the recipient, and the therapeutic activity of the particular composition.

Given that the FGF1 and FGF2 polypeptides of the present invention confer greater resistance to proteases and higher biological activity, it is envisioned that compositions including or encoding such polypeptides would be useful in several different FGF applications.

In some embodiments, the "FGF compositions" (the FGF1 or FGF2 compositions) described herein (either individually or in combination) may be used to treat diabetes (i.e., type 1 or type 2). Treatment of type1 and type2 diabetes may be achieved by injecting the FGF compositions (either individually or in combination). Without being limited by theory, systemic FGF polypeptides could potentially activate the process of angiogenesis. Also the skeletal muscle cell multiplication drastically increases that could result in large uptake of blood glucose eventually restore the pancreas to function normally.

In some embodiments, the FGF compositions described herein (either individually or in combination) may be used to treat internal injuries. Because the disclosed FGF polypeptides demonstrated protease resistant activity, they may be used in treating visceral injuries such as intestinal wall ruptures (sites with excess protease action like trypsin etc.).

In some embodiments, the FGF compositions described herein (either individually or in combination) may be used in cosmetic applications. For example, a medicinal composition including the FGF compositions described herein (either individually or in combination) and FGF2, FGF5, FGF7 and/or FGF10 could be used in various cosmetic applications including, without limitation, whitening, anti-crinkle and anti-aging related problems.

In some embodiments, the FGF compositions described herein (either individually or in combination) may be used to treat cardiovascular disorders. It has been shown that injection of FGF-1 into the intramyocardial region resulted in improved collateral artery growth and capillary formation and proliferation. Thus, the FGF compositions (either individually or in combination) may be used to improve collateral artery growth and capillary formation and proliferation.

In some embodiments, the FGF compositions described herein (either individually or in combination) may be used to treat critical limb ischemia. For example, gene therapy based delivery of FGF polypeptides (either individually or in combination) could be used in treating end stage limb ischemia which would potentially reduce the chances of amputation.

In some embodiments, the FGF compositions described herein (either individually or in combination) may be used in treating nerve injuries. The disclosed FGF compositions (either individually or in combination) could be used to regenerate damaged cells in the spinal cord.

In some embodiments, the FGF compositions described herein (either individually or in combination) may be used to treat burns. Several factors are responsible for causing burns such as heat, electricity, UV-light and corrosive chemicals. The disclosed FGF compositions (either individually or in combination) might quicken the process of healing of burns along with other pharmacologically active ingredients.

In some embodiments, the FGF compositions described herein (either individually or in combination) may be used in hydrogels. Hydrogels including the disclosed FGF compositions (either individually or in combination) could be used in design and development of scaffolds in the fields of tissue engineering and regenerative medicine.

In some embodiments, the FGF compositions described herein (either individually or in combination) may be used in regenerating hair growth. Growth factors like FGF1, FGF2, and FGF10 are known to be involved in the regulation of hair morphogenesis and hair growth. Due to the enhanced bioactive properties of the disclosed FGF compositions, the disclosed FGF compositions may be used to alter (increase or decrease) hair growth.

In some embodiments, the FGF compositions described herein (either individually or in combination) may be used to treat wounds. For example, compositions including Parathyroidharmone (PTH), Collagen binding protein (CBD), and the disclosed FGF compositions (either individually or in combination) could be used in the treating both chronic and acute wounds.

In some embodiments, the FGF compositions described herein (either individually or in combination) may be used to repair an injured retina. The disclosed FGF compositions (either individually or in combination) may be used for rejuvenating damaged cells of the retina such as in retinopathy disorders.

In some embodiments, the FGF compositions described herein (either individually or in combination) may be used in skeletal muscle development. For example, the disclosed FGF compositions (either individually or in combination) could be fused to other FGF family members that could facilitate the faster growth of skeletal muscle.

In some embodiments, the FGF compositions described herein (either individually or in combination) may be used in cell cultures such as mammalian cell cultures.

In some embodiments, the FGF compositions described herein (either individually or in combination) may be used to treat arterial diseases. For example, the disclosed FGF compositions (either individually or in combination) may be used in treatment of peripheral arterial disease with intermittent claudication.

In some embodiments, the FGF compositions described herein (either individually or in combination) may be used to treat aging related disorders.

In some embodiments, the FGF compositions described herein (either individually or in combination) may be used to regenerate internal organs.

In some embodiments, the FGF compositions described herein (either individually or in combination) may be used to treat osteoporosis.

In some embodiments, the FGF compositions described herein (either individually or in combination) may be used to treat gastric ulcers.

In some embodiments, the FGF compositions described herein (either individually or in combination) may be used to treat colitis such as ulcerative colitis. For example, the disclosed FGF compositions (either individually or in combination) may be used in combination with keratinocyte growth factor-1 to treat ulcerative colitis.

In some embodiments, the FGF compositions described herein (either individually or in combination) may be used to treat scars developed from various types of injuries.

In some embodiments, the FGF compositions described herein (either individually or in combination) may be used in combination with biopolymers such as carboxyl methyl benzylamine dextran sulfonate to treat digestive tract ulcers.

In some embodiments, the FGF compositions described herein (either individually or in combination) may be used to affect differentiation of osteoblast cells. For example, the disclosed FGF compositions (either individually or in combination) may be used, for example by gene therapy, to enhance the down regulation of Wnt signaling proteins which would result in decreased differentiation of osteoblast cells.

In some embodiments, the FGF compositions described herein (either individually or in combination) may be used to treat damaged tissue due to radiation or chemotherapy. For example, the disclosed FGF compositions (either individually or in combination) may be used in combination with FGF-20 to treat damaged tissue due to radiation and also due to extensive use of chemotherapy.

In some embodiments, the FGF compositions described herein (either individually or in combination) may be used to treat diabetes and obesity. For example, FGF-21 controls the glucose-uptake of adipocytes independent of insulin which would decrease the load of blood glucose, triglycerides and glucagon. Thus, compositions including the FGF compositions described herein (either individually or in combination) and FGF-21 would be used in treating diabetes and obesity.

In some embodiments, the FGF compositions described herein (either individually or in combination) may be used to treat disorders related to energy homeostasis. For example, the disclosed FGF compositions (either individually or in combination) may be used in combination with FGF8 to treat disorders of energy homeostasis such as obesity, dyslipidemia, diabetes, insulin resistance, hyperglycemia or the metabolic syndrome.

In some embodiments, the FGF compositions described herein (either individually or in combination) may be used to control differentiation of cord cells. For example, the disclosed FGF compositions (either individually or in combination) may be used in combination with FGF4 to induce human umbilical cord mesenchymal stem cells to differentiate into hepatocytes.

In some embodiments, the FGF compositions described herein (either individually or in combination) may be used to treat alopecia. For example, the disclosed FGF compositions (either individually or in combination) may be used in combination with FGF-10 to treat alopecia.

In some embodiments, the FGF compositions described herein (either individually or in combination) may be used to treat osteoarthritis. For example, the disclosed FGF compositions (either individually or in combination) may be used in combination with FGF-9 to promote cartilage repair in patients suffering from osteoarthritis by reducing the abnormal differentiation of articular cartilage cells at the site of inflammation.

In some embodiments, the FGF compositions described herein (either individually or in combination) may be used to treat acute renal failure. For example, the disclosed FGF compositions (either individually or in combination) may be used in combination with inhibin beta and FGF-2 to treat acute renal failure.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1

Development of Super FGF

The amino acid sequence of the FGFs, including hFGF1, folds into a β-trefoil conformation. This group of cytokines exhibits a wide array of activities such as, mitogenic activity, angiogenic activity, wound healing, and bone growth. The inherent instability of FGFs under physiological conditions and their susceptibility to the action of proteolytic enzymes (such as thrombin) is primarily due to the repulsions among the positively charged resides located in the heparin binding pocket. Under in vivo conditions, the stability for these proteins is enhanced through electrostatic interactions with the negatively charged cell surface glycosaminoglycans (GAGs), heparin, or heparan sulfate (HS). The FGF-heparin interaction stabilizes the structure of FGF, including the human acidic fibroblast growth factor (hFGF1) by decreasing the repulsion(s) between the positively charged residues located in the heparin binding pocket.

Typically, the structural stability of hFGF1, gained through its interactions with heparin, is beneficial because it increases the in vivo stability of the growth factor. However, heparin binding affinity of hFGF1 can be a significant disadvantage in healing topical wounds. For example, at the wound site, multiple groups of biologically important molecules function together to repair the tissue damage. The first line of action after an injury is to block the loss of blood by the clotting mechanism which involves the key proteolytic enzyme, thrombin, which converts fibrinogen to fibrin. Interestingly, thrombin is also a strong heparin binding protein. Research on wtFGF1 confirmed that thrombin can cleave at position R136 of hFGF1 and inactivate its function. Even though there are reports about the positive effects of endothelial cell repair under in vitro conditions, clinical studies showed that the presence of exogenous heparin delayed the healing process of burns and diabetic foot ulcers (Galvan, 1996). This could be due to the decreased bioavailability of FGFs that are bound to the GAG molecules. In general, it is believed that the high binding affinity of hFGf1 to heparin potentially increases the probability of thrombin, a heparin binding protein, to gain access to hFGF1 and cause degradation of the growth factor. Therefore, in this context, generation of bioactive hFGF1 variants that completely lack heparin binding may significantly decrease its susceptibility to thrombin cleavage.

Figure 1B:
Figure 3:
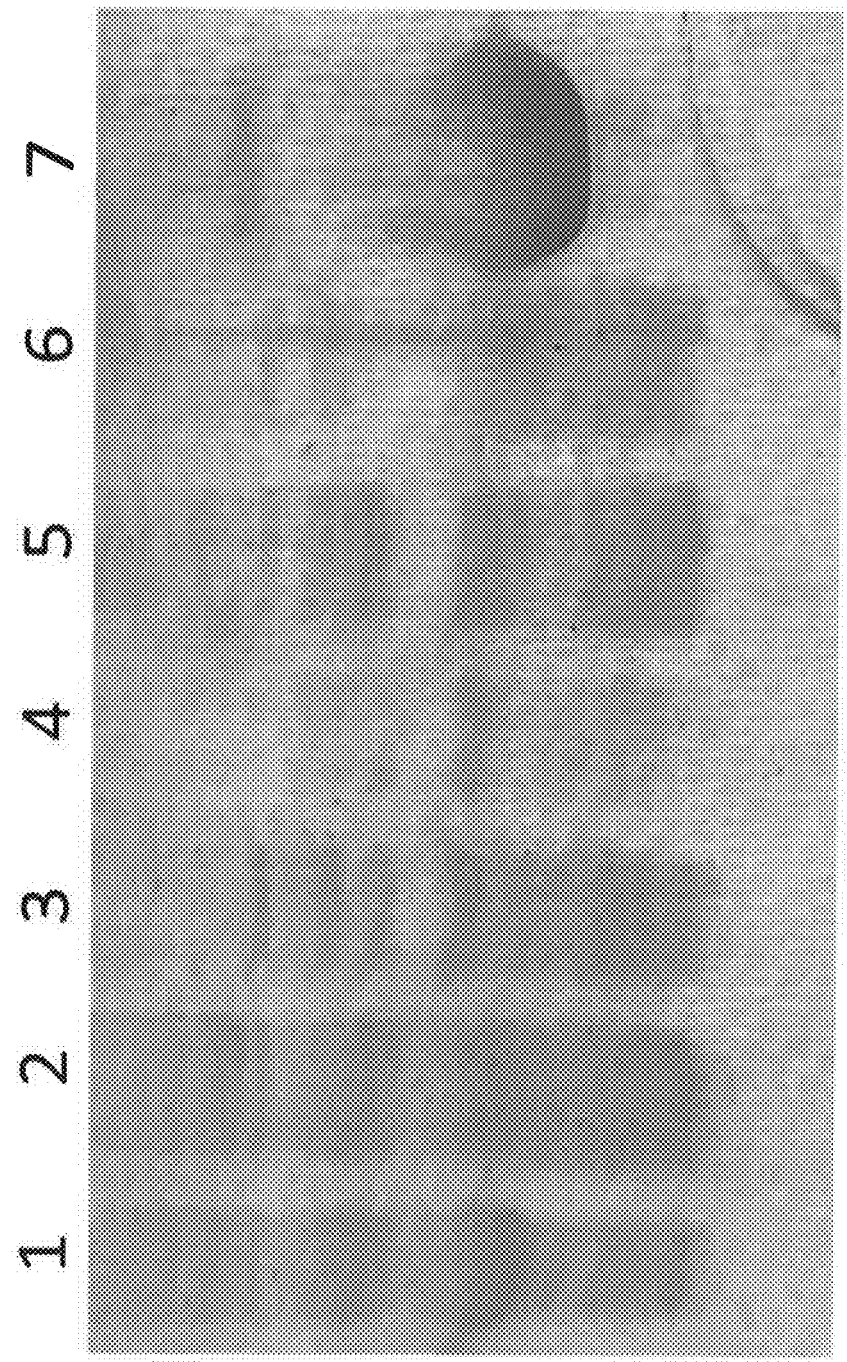
FIG. 3 shows purification of wt hFGF1 protein on heparin Sepharose. Lanes 1—Supernatant; 2—Flow through; 3—100 mM NaCl; 4—300 mM NaCl; 5—500 mM NaCl; 6—800 mM NaCl; 7—1500 mM NaCl.
Figure 4:
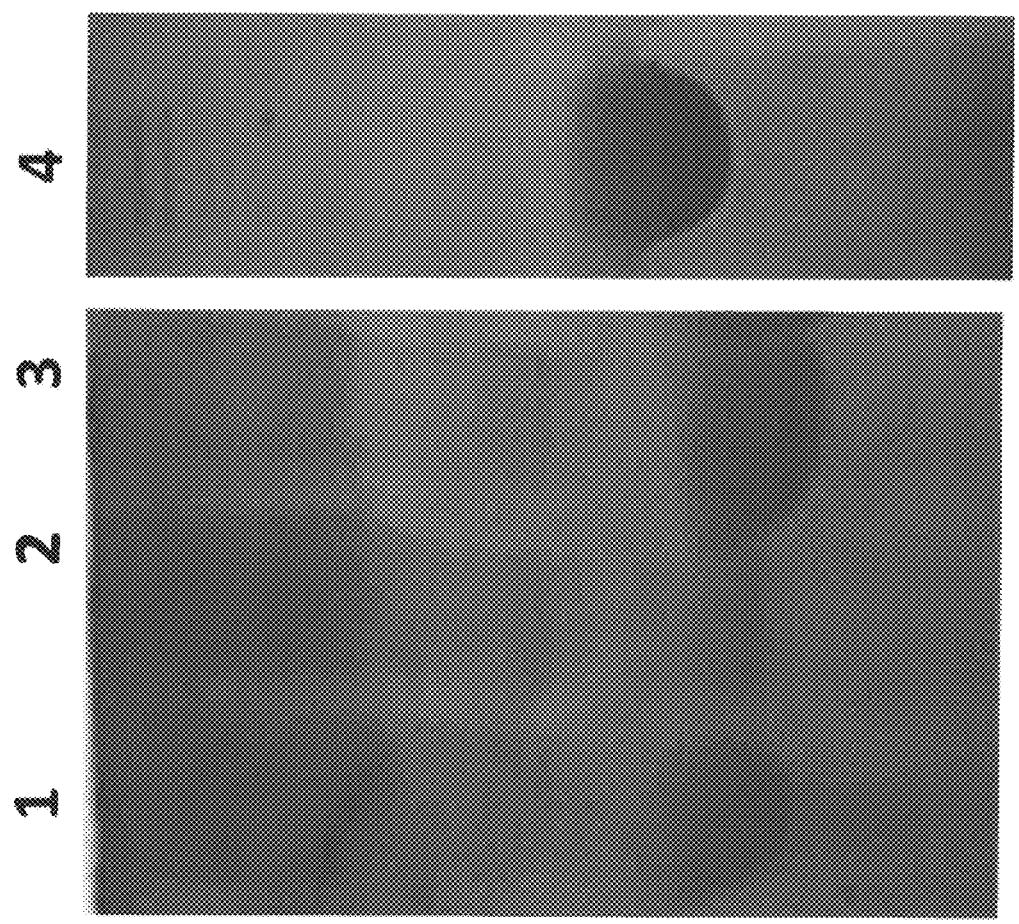
FIG. 4 shows purification of super hFGF1 protein on heparin Sepharose. Lanes 1—Supernatant; 2—Flow through; 3—Buffer wash; 4—Post-dialysis.
Figure 5:
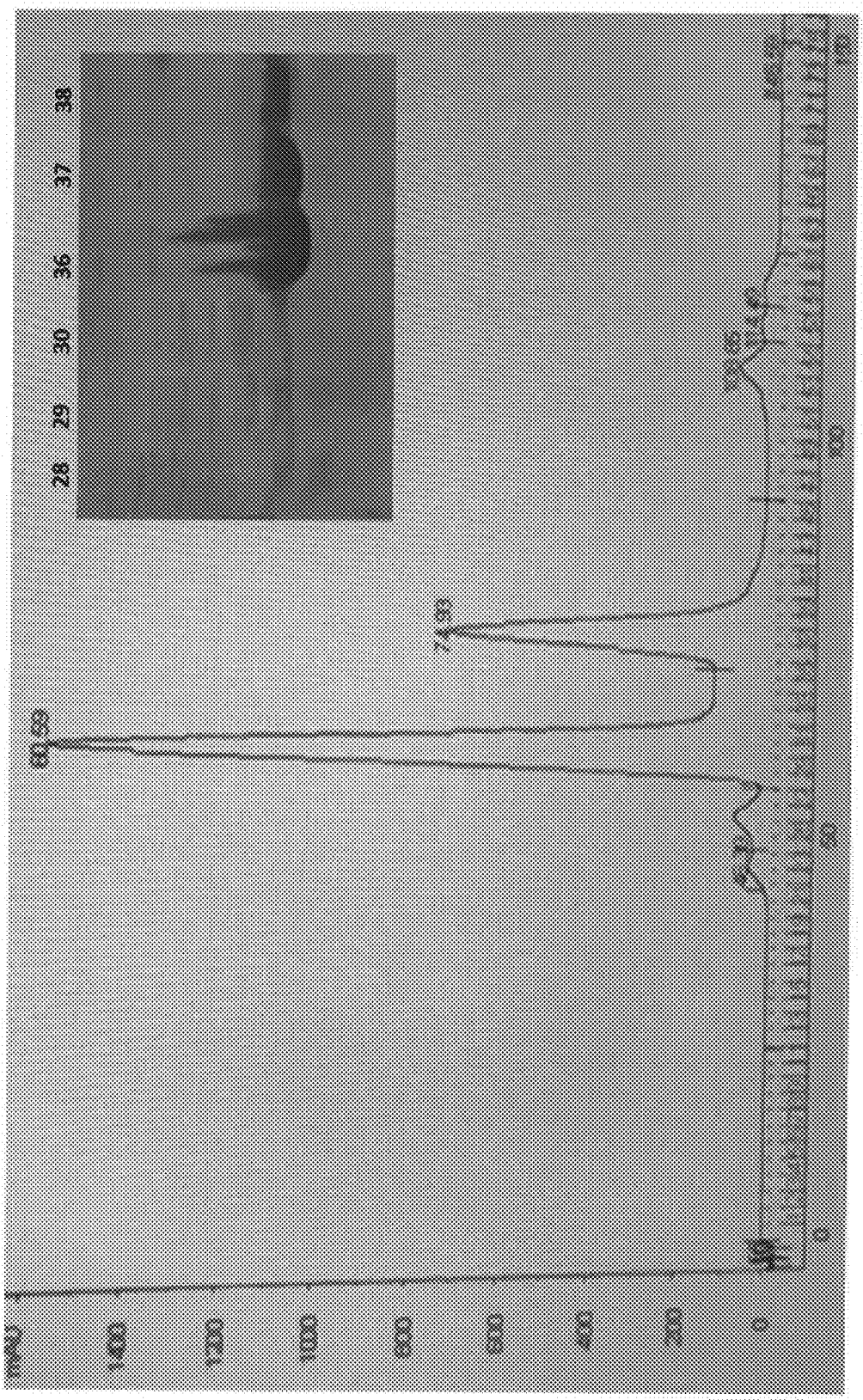
FIG. 5 shows purification of super hFGF1 on HiPrep Superose S-75 connected to Akta FPLC. Inset figure shows the SDS-PAGE with fractions showing the pure super hFGF1 in fractions 36-38.
Figure 7B:
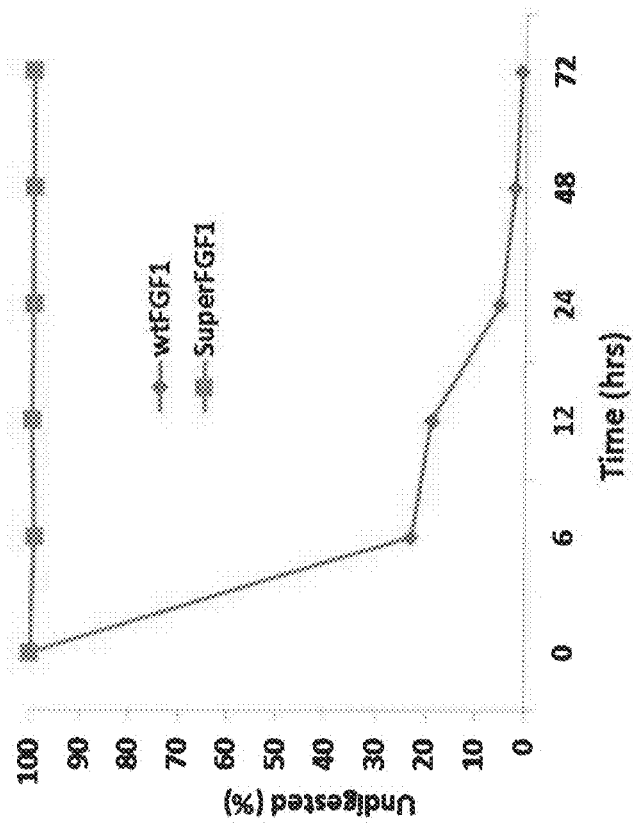
FIG. 7B—densitometric data obtained from SDS-PAGE gels was plotted with Time (min) on X-axis and Undigested (%) on Y-axis.
Figure 7A:
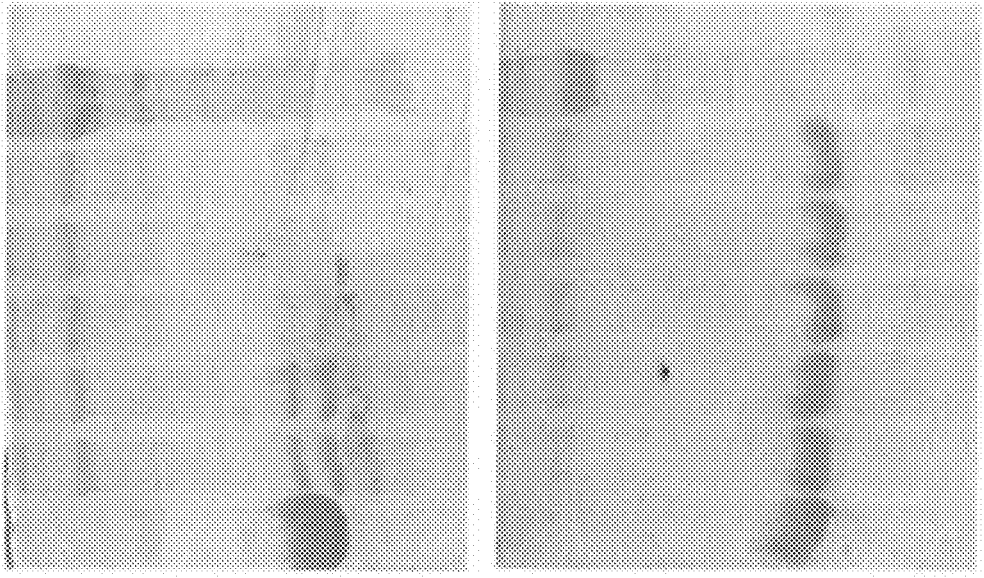
FIG. 7A shows SDS-PAGE showing the thrombin cleavage of wt hFGF1 (Upper) and super hFGF1 (lower) respectively. Lanes 1—0 min, 2—10 min, 3—15 min, 4—30 min, 5—45 min, 6—60 min and 7—pure trypsin.
Figure 8:
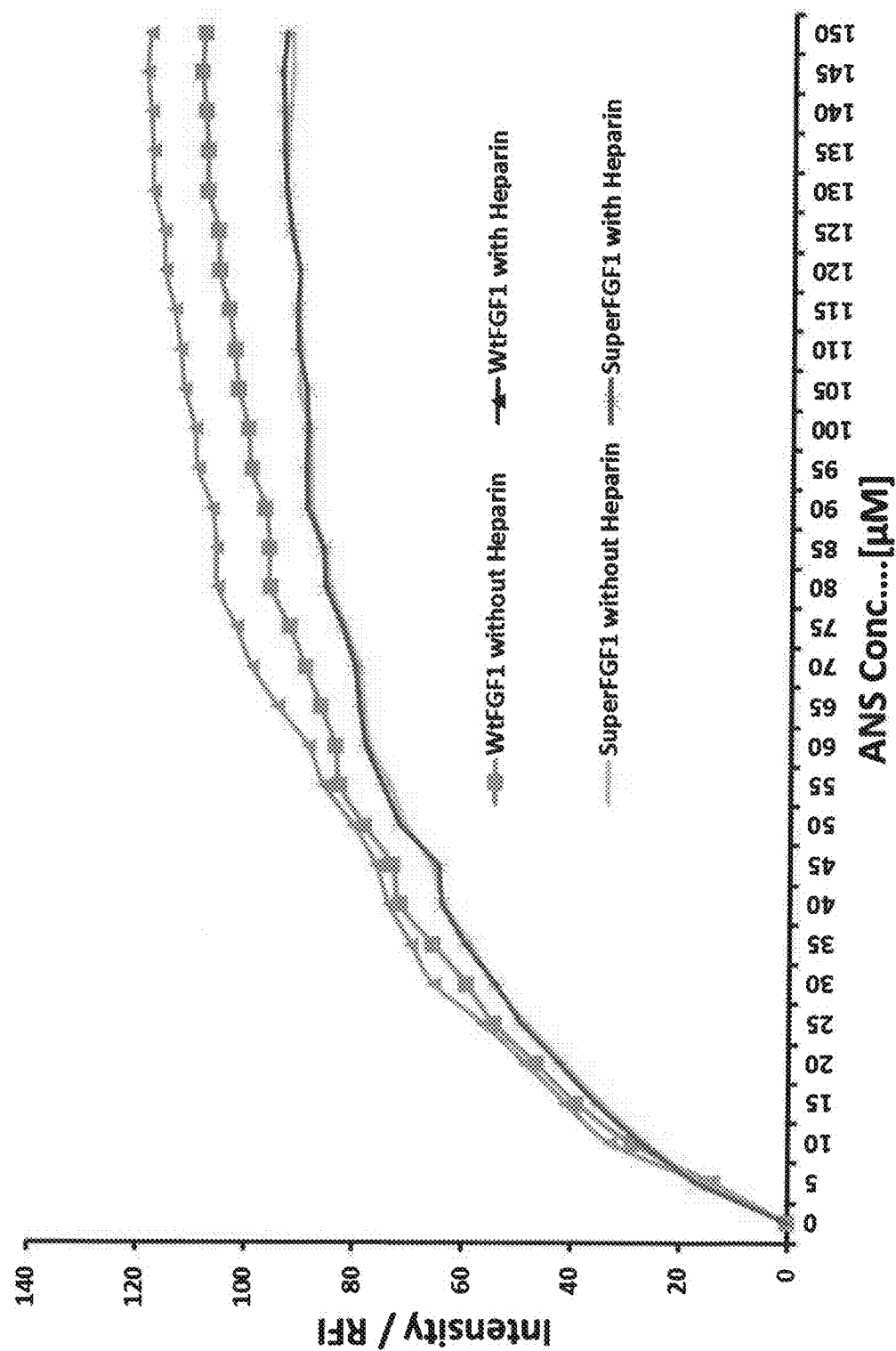
FIG. 8 shows an ANS binding assay, in the absence and presence of heparin, for wt-hFGF1 and super hFGF1. A stock ANS solution was added at 2 μM increments to the protein solutions and the sample was excited at 380 nm the emission fluorescence intensity was measured at 500 nm.
Figure 9:
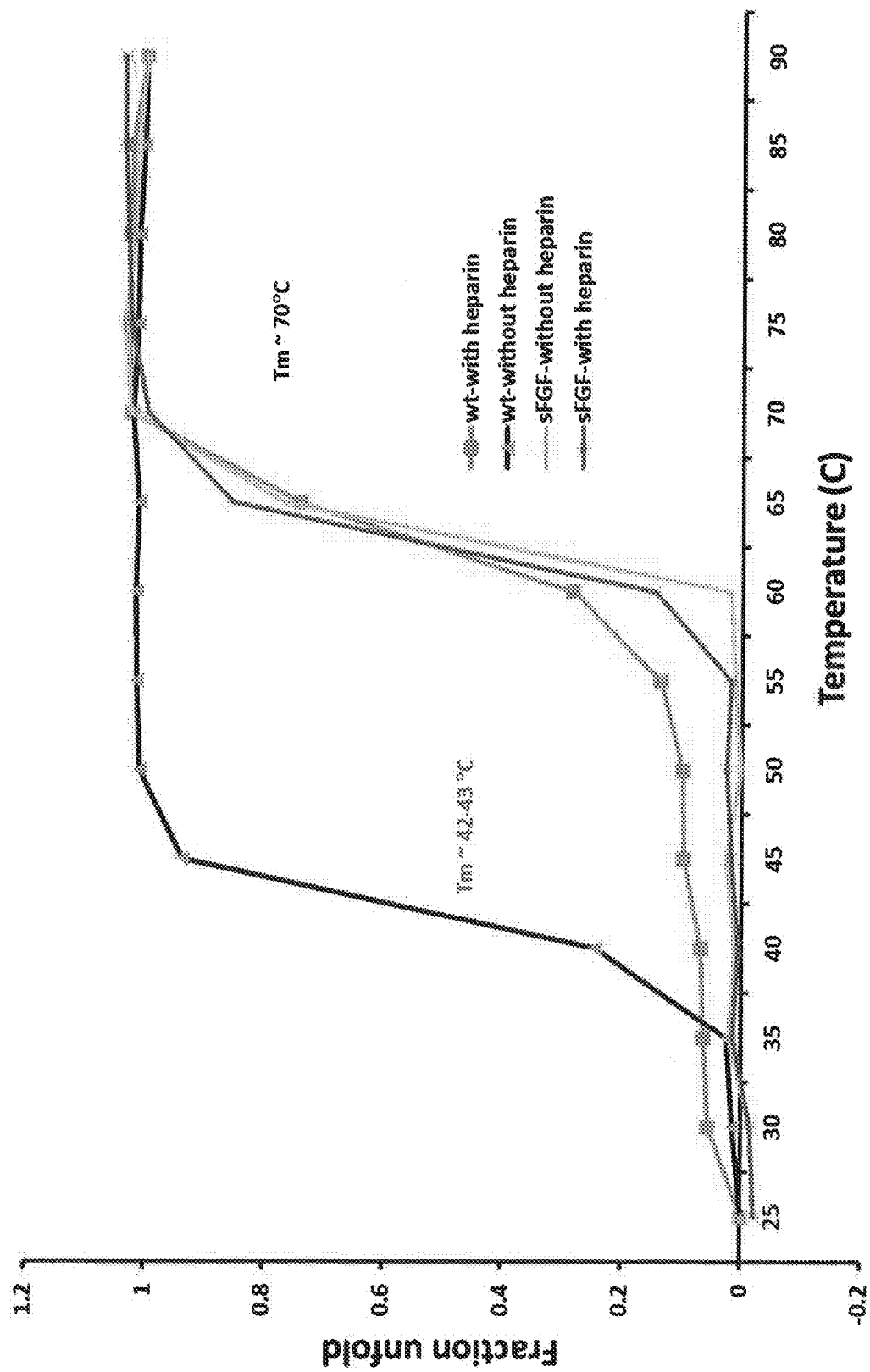
FIG. 9 shows temperature-induced unfolding of wt and super hFGF1 in the absence and presence of heparin. Protein samples were subjected to heat treatment with increments of 5° C. Ratio of relative fluorescence intensity at 308 nm and 350 nm were used to calculate the fraction unfolded. A plot of temperature versus fraction unfolded yields the melting temperature ($T_m$) for the respective protein samples.
Figure 10:
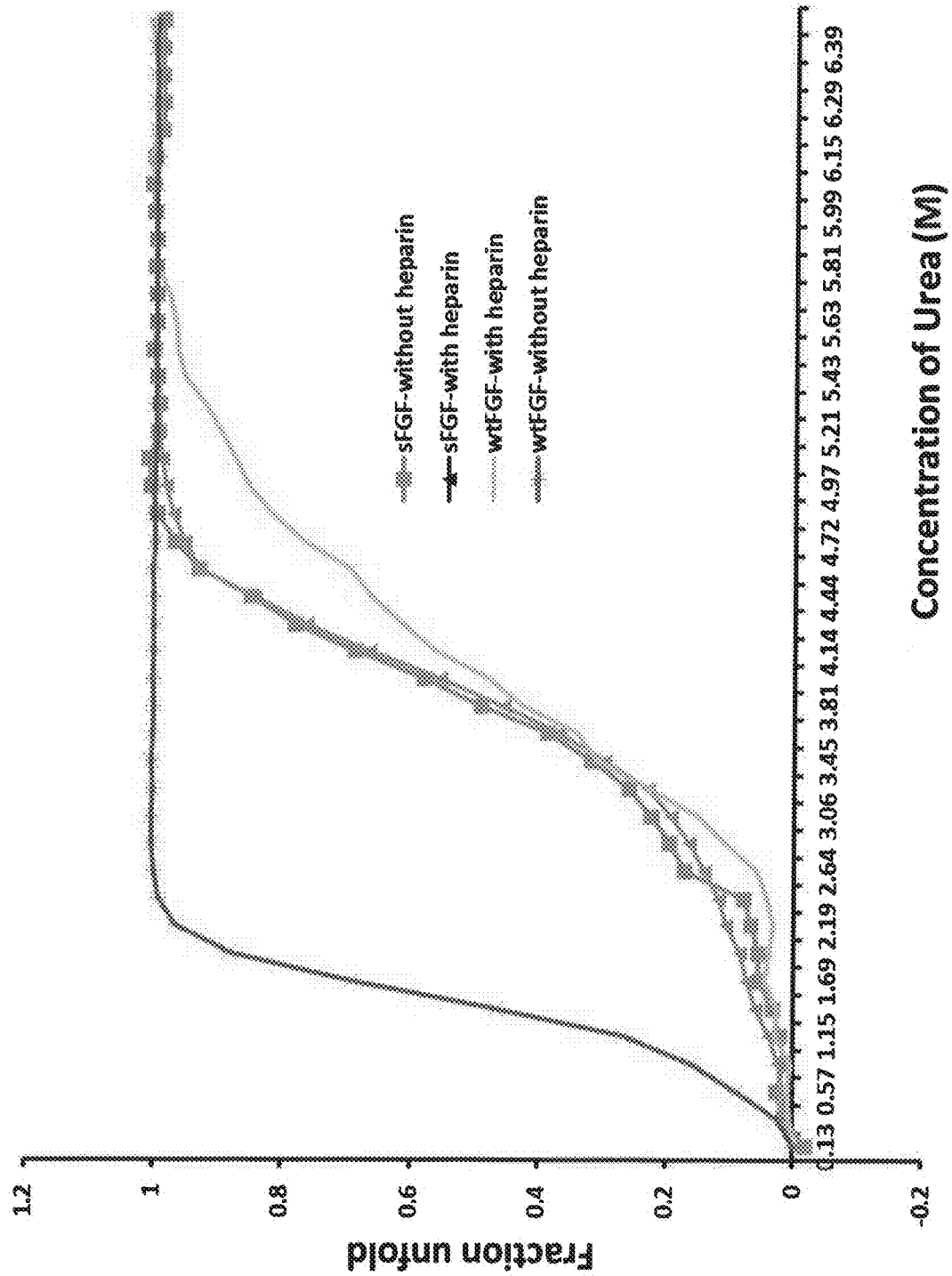
FIG. 10 shows urea-induced unfolding of wt-hFGF1 and super hFGF1 in the absence and presence of heparin. Protein samples were titrated with increments of denaturant. Ratio of relative fluorescence intensity at 308 nm and 350 nm was used to calculate the fraction unfolded. A plot of temperature vs fraction unfolded yield the melting temperature ($T_m$) for the respective protein samples.
Figure 11:
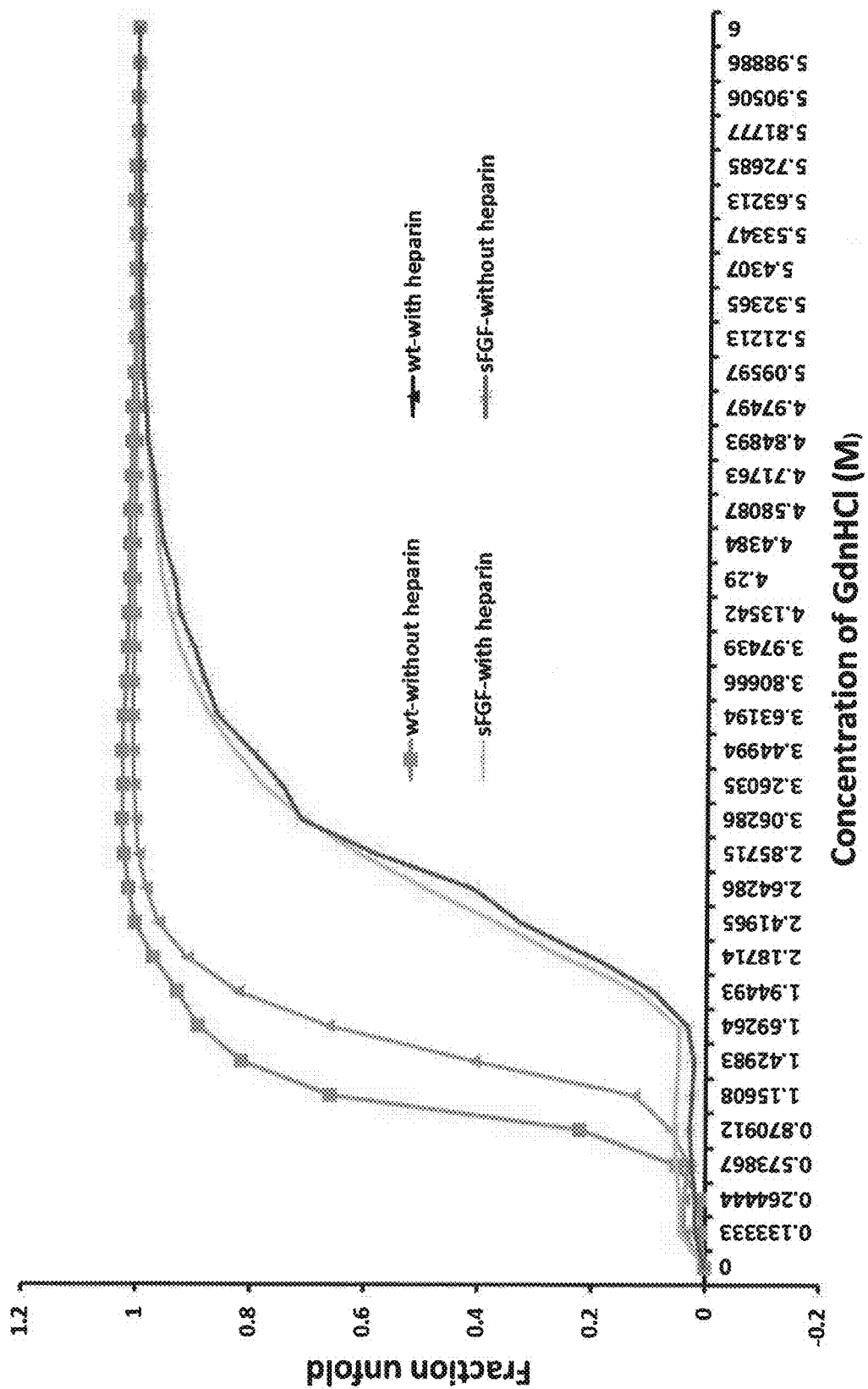
FIG. 11 illustrates the urea-induced unfolding of wt-hFGF1 (SEQ ID NO: 1) and super-hFGF1 (SEQ ID NO: 2), in the absence and presence of heparin. Protein samples were titrated with increments of denaturant. Ratio of relative fluorescence intensity at 308 nm and 350 nm was used to calculate the fraction unfolded. A plot of temperature vs fraction unfolded yield the melting temperature (Tm) for the respective protein samples.
Figure 12:
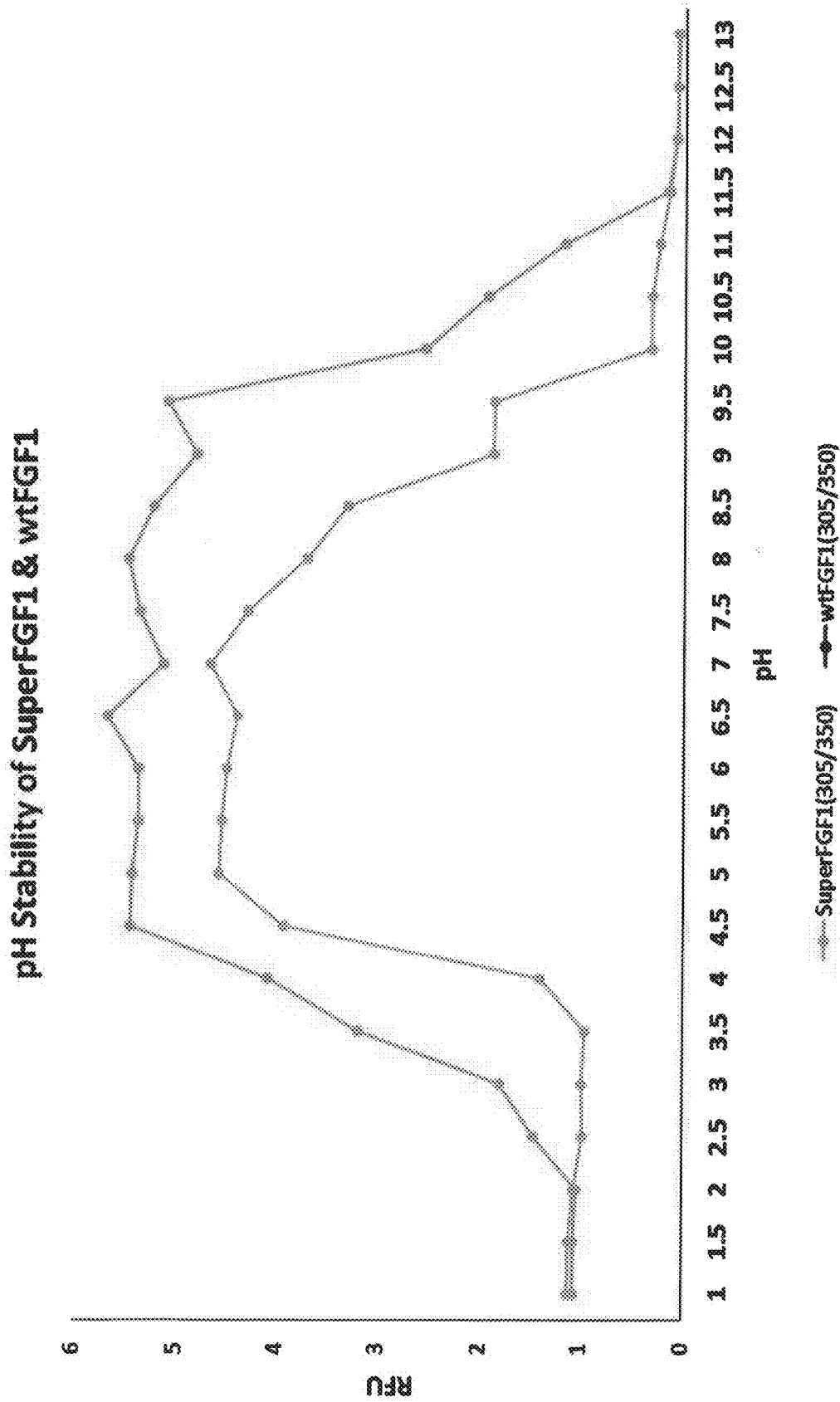
FIG. 12 illustrates the effect of pH on the stability of wt-hFGF1 and Super hFGF1. Ratio of emission fluorescence at 308 to 350 nm was plotted against varied pH to estimate the stability of proteins.
Figure 14:
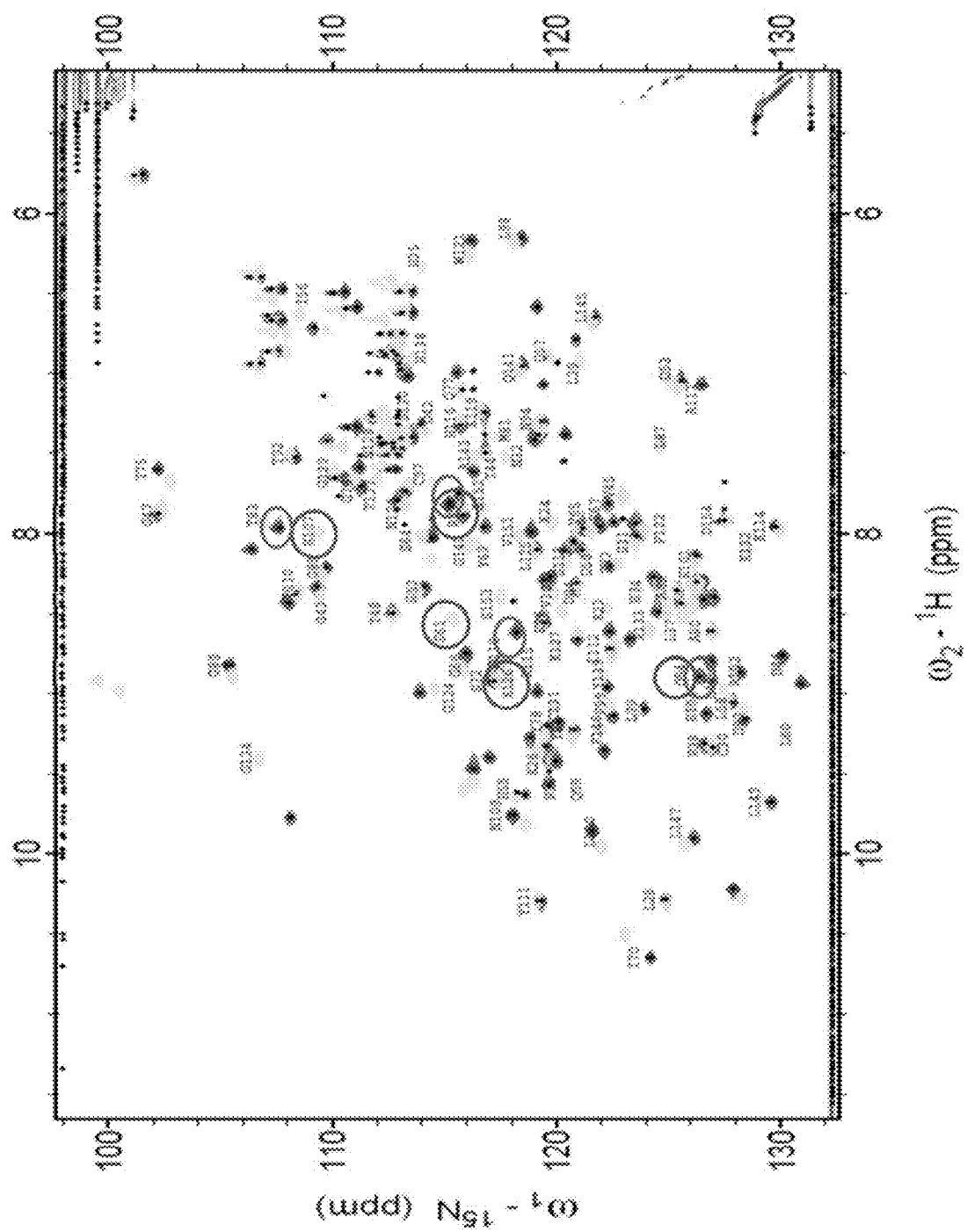
FIG. 14 shows an overlay of the $^1$H-$^{15}$N HSQC of wild type hFGF1(yellow) and the super hFGF (red). The blue circles represent the amino acids in wild type (R at $136^{th}$, Q at $54^{th}$, K at $126^{th}$, S at $61^{st}$, and H at $107^{th}$ position). The green circles are the predicted location of the amino acid after the mutation.
Figure 15:
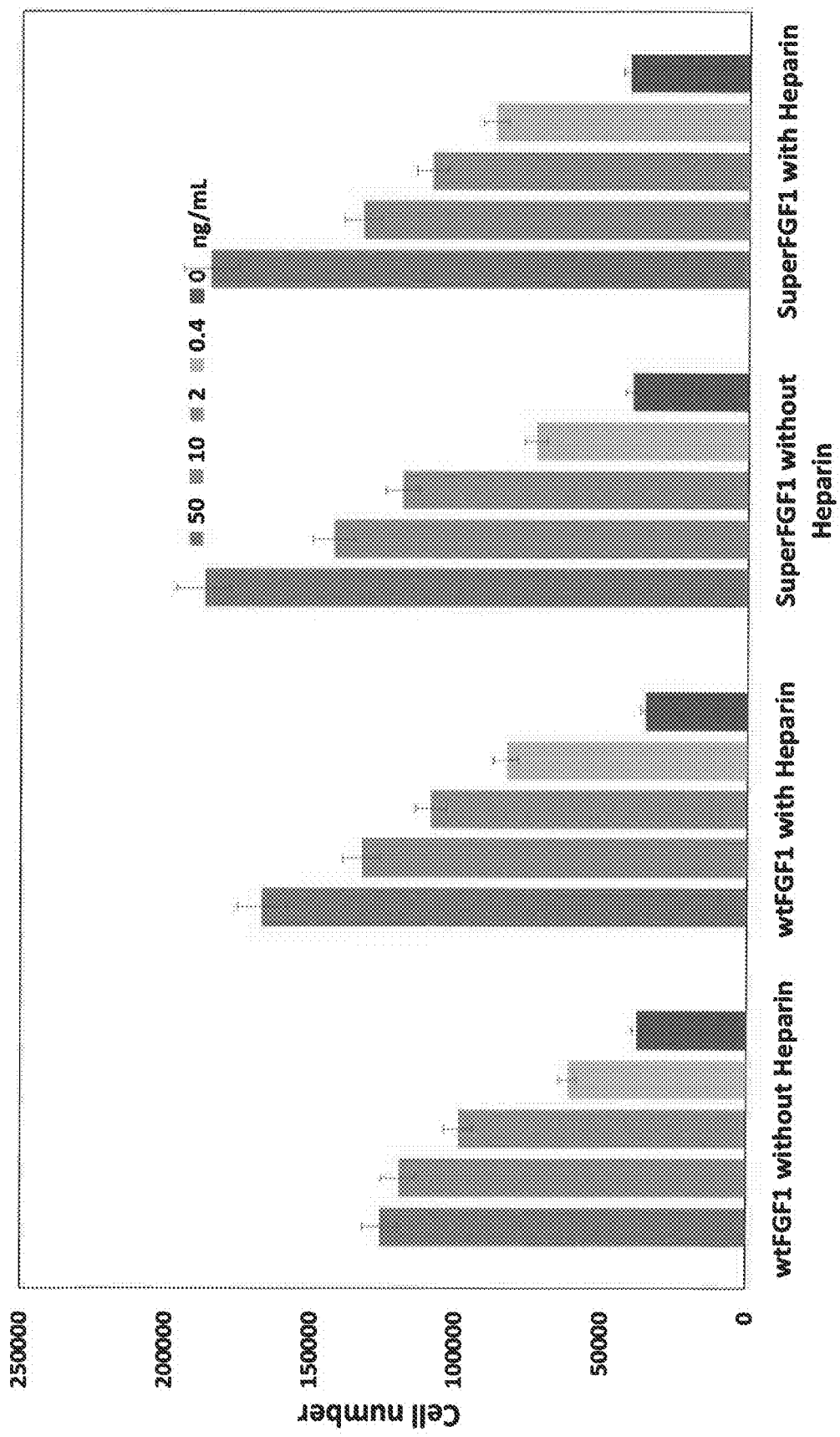
FIG. 15 shows a cell proliferation assay of wt-hFGF1 and super hFGF1, in the absence and presence of heparin. Actively growing NIH-3T3 cells were adapted to serum deprivation followed with addition of different concentration of the mitogen. Cell number was quantified using GloSensor™ cAMP assay as per manufacturer's instructions.
Figure 16B:
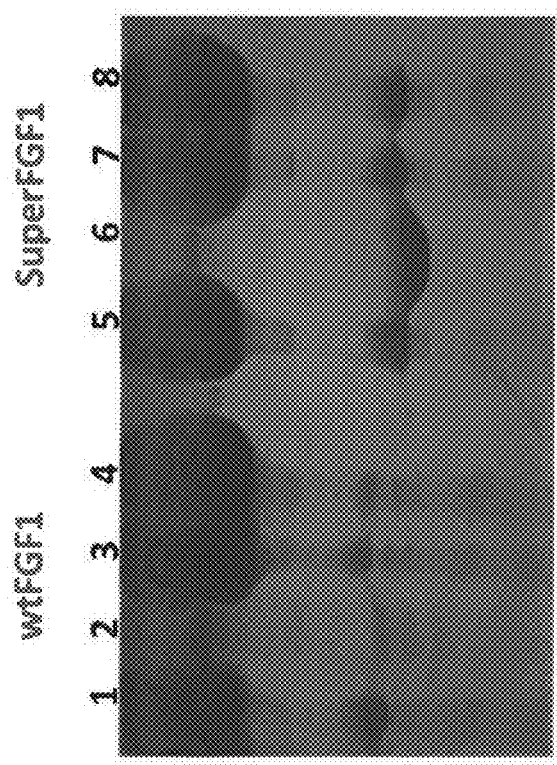
FIGS. 16A-16B illustrate the effect of culture medium on the ability of wt-hFGF1 and super hFGF1.
Figure 16A:
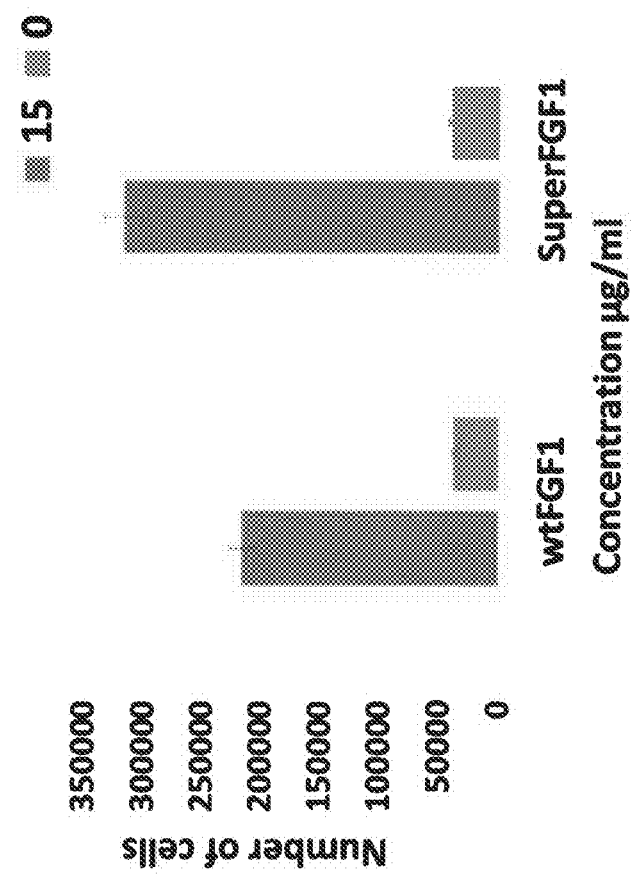
Figure 17:
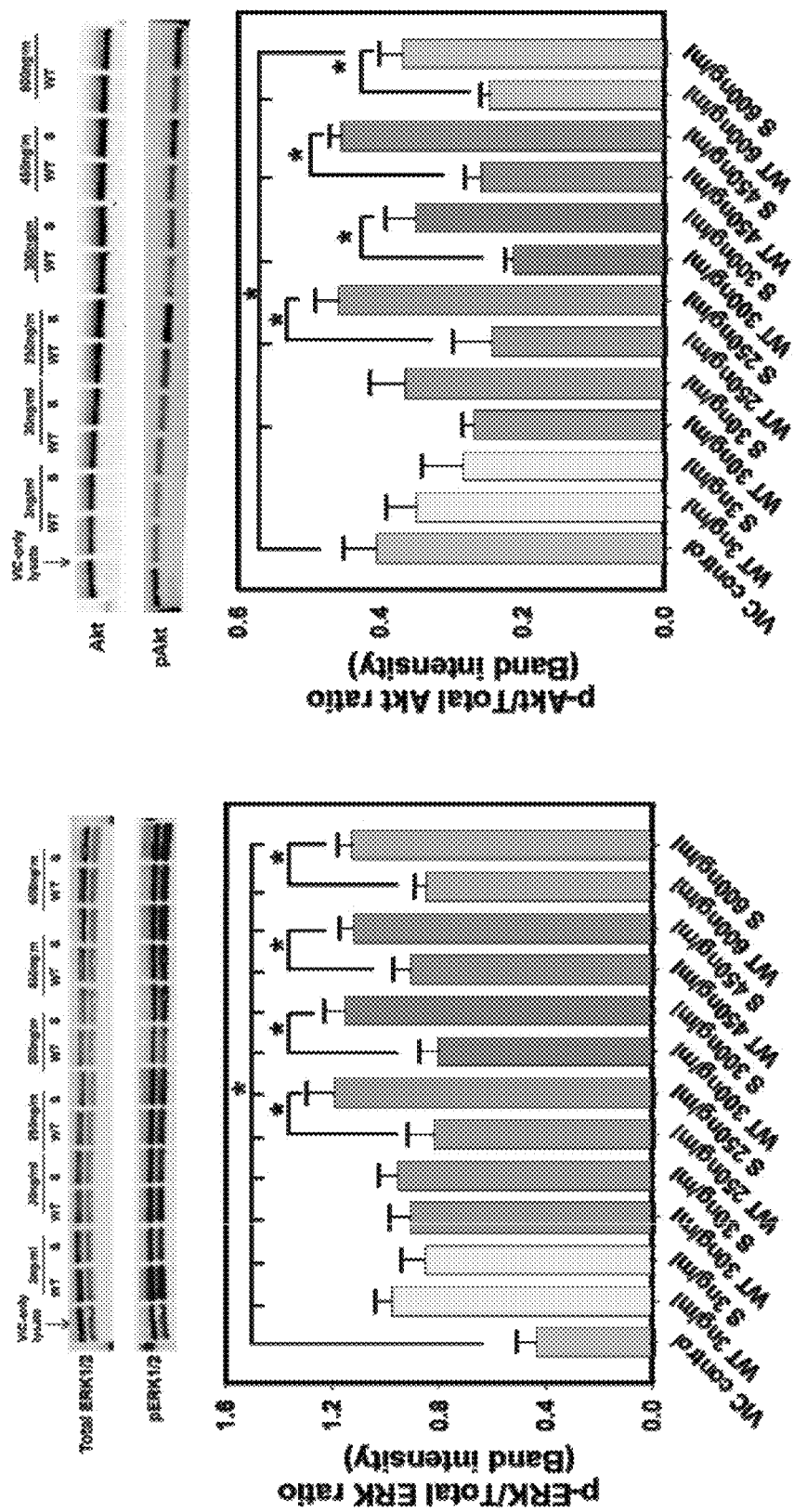
FIG. 17 shows serum starved valve interstitial cells (VICs) treated with different concentrations of wt-hFGF1 and super hFGF1 (3 ng/ml-600 ng/ml). Cell lysates were resolved on SDS-PAGE followed with western blotting to detect the expression pattern of phosphaorylated ERK1/2 (left panel) and phosphorylated Akt proteins (right panels).
Figure 18:
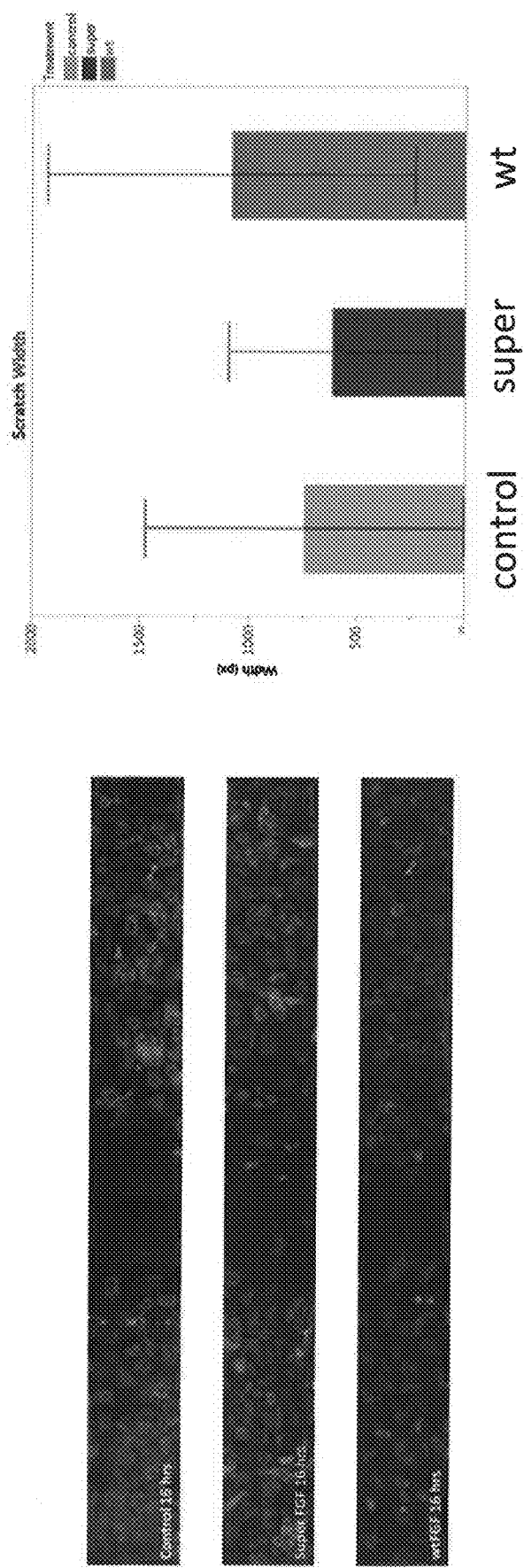
FIG. 18 illustrates the scratch assay to confirm the efficiency of superFGF1 in fibroblast cell proliferation. Coriell AG21264 cells were grown to confluence as monolayer, a uniform scratch was made in the center. Cells were incubated with samples of wt-hFGF1 and super hFGF1 along with controls, and scratch width was measured. Each error bar is constructed using 1 standard deviation from the mean.
Figure 19:
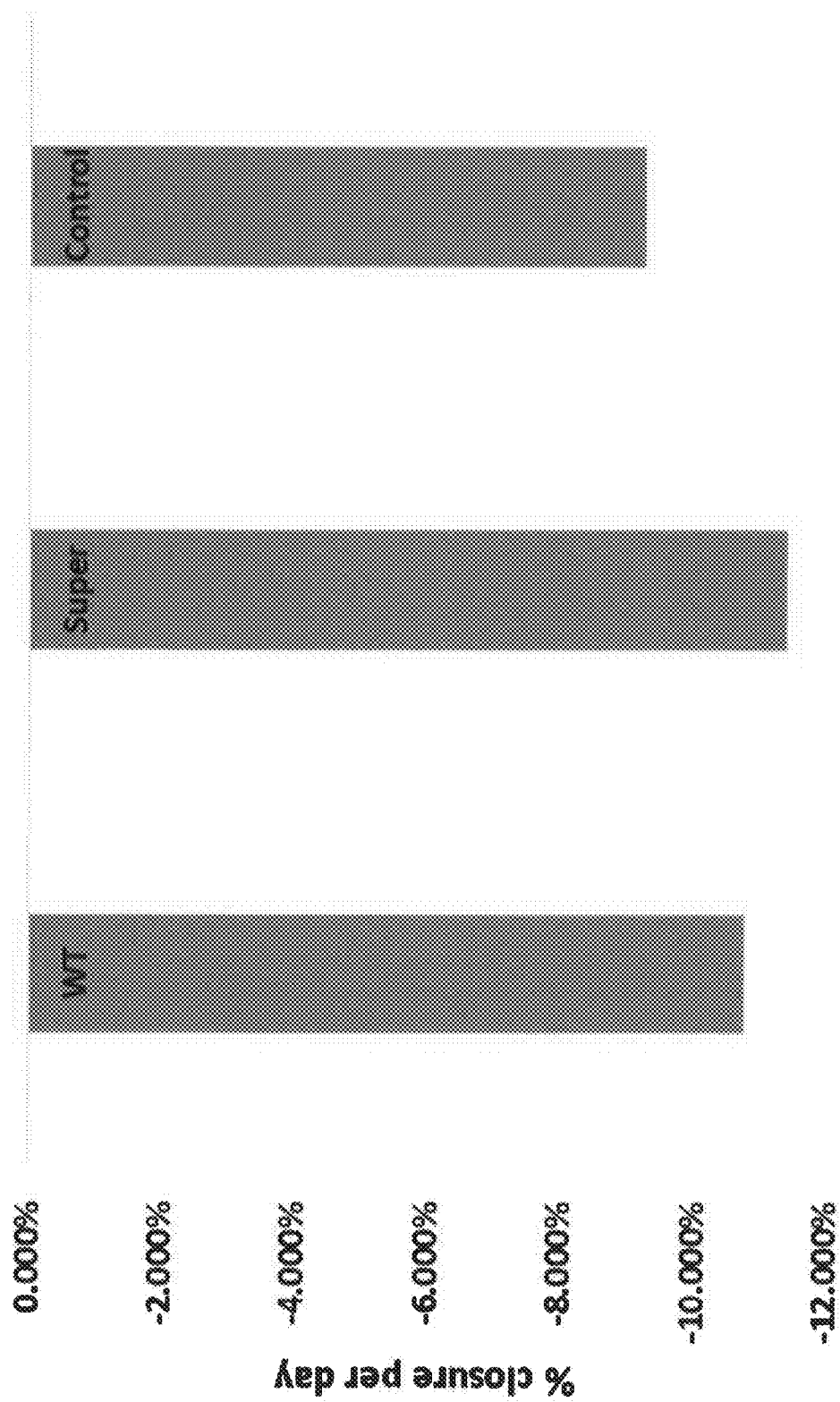
FIG. 19 illustrates the effect of FGFs on the rate of wound closure. Male C57Bl/6J mice (12 weeks old) were given 6 mm diameter full-thickness excisional skin wounds. Samples of wt-hFGF1 and super hFGF1 were applied topically and the rate of closure was monitored for 3 days. The data was plotted as percent closure/day.

This example is focused on the design and development a novel engineered form of FGF1 with properties of enhanced thermal stability and shelf life, resistance to proteolytic activity, and heparin independent bioactivity. Based on the available literature on the structure-activity relationship of hFGF1 and the information gained from the three-dimensional structure, we used protein engineering techniques to generate a super hFGF1 variant (Q41P S48L H94S K113N R123E, FIGS. 1A-1B and FIG. 2; wild-type hFGF1 is SEQ ID NO: 1 and the super hFGF1 is SEQ ID NO: 2). The nucleotide and protein sequence corresponding to the mutant plasmid was verified by DNA sequencing as shown in FIG. 2.

Purification of recombinant wt-hFGF1 (SEQ ID NO: 1) and super hFGF1 (SEQ ID NO: 2) was performed using heparin sepharose column chromatography wherein the wt hFGF1 protein eluted at a higher salt concentration (>1200 mM NaCl, (FIG. 3). Interestingly super FGF1 (SEQ ID NO: 2) did not show any affinity to bind to the heparin Sepharose column and eluted in the wash buffer. In fact, the binding affinity of super hFGF1 is weaker than that of non-heparin binding proteins which non-specifically bind to the affinity resin (FIG. 4). The super FGF1 was further purified by subjecting it to a size exclusion chromatography which yielded two peaks—the first major peak corresponding to a high molecular weight bacterial contaminating protein(s) followed by a second peak representing super hFGF1 (FIG. 5).

The shelf life of super hFGF1 (SEQ ID NO: 2) was monitored at room temperature (at 25° C.) by SDS PAGE over a period of 3 months. Super hFGF1 was not degraded during this time period and there was no discernable loss in the cell proliferation activity even after proteolytic resistance of wt hFGF1 and super hFGF1 were determined by performing limited trypsin digestion and extended thrombin cleavage (FIGS. 6A-6B and FIGS. 7A-7B). Surprisingly, super hFGF1 showed complete resistance against proteolytic enzymes such as, trypsin and thrombin.

Changes in the surface hydrophobicity were measured by 8-Anilinonaphthalene-1-sulfonic acid (ANS) binding. Comparison of the saturating curves between the wtFGF1 and superFGF1 in the absence and presence of heparin, shows that very little solvent-accessible surface hydrophobicity on the surface is available in super hFGF1 unlike wt-FGF1 which shows a greater exposure of the hydrophobic surface(s) to the solvent (FIG. 8).

Stability against temperature and the denaturants can be directly related to the half-life of a protein sample hence molecules exhibiting higher $T_m$ and $C_m$ values are expected to exhibit biological activity at physiological temperature for an extended period of time. Super hFGF1 (SEQ ID NO: 2) exhibited much higher thermal stability (Tm~70° C.) compared to that of wthFGF1 (SEQ ID NO: 1) both in the absence and presence of heparin (FIG. 9). A similar trend was observed even in case of chemical-induced denaturation with urea (~3.5M) and Guanidium chloride (GdnCl) (2.6M) (FIGS. 10 and 11).

Stability of super FGF1 was examined under different pH conditions. Compared to the wtFGF1, super hFGF1 (SEQ ID NO: 2) exhibited enhanced pH stability under both acidic and alkaline environments spanning from pH 3 through 11 (FIG. 12).

Isothermal calorimetric assay was used to determine the binding affinity of wt-FGF1 and super hFGF1 samples to heparin. Heparin binding was completely abolished in super hFGF1 (SEQ ID NO: 2) unlike wtFGF1 (SEQ ID NO: 1) which exhibits a relatively high heparin binding affinity of ~2 μM (FIGS. 13A-13B).

Changes in the structure of wt-FGF1 and super hFGF1 were determined using $^1H$ $^{15}N$ HSQC multidimensional NMR spectroscopy. Significant perturbations of the amino acids in proximity to the mutation sites were observed. Interestingly, residues D53 and H55, neighboring P54 did not show significant chemical shift perturbation. Overall, the engineered mutations to generate super hFGF1 did not significantly change the gross three-dimensional structure of the protein (FIG. 14).

Biological activity and stability against the proteases present in the culture medium was tested in the absence and presence of heparin. wt-hFGF1 showed greater heparin dependence compared to super hFGF1 (FIG. 15). wt hFGF1 was found to be completely degraded at 37° C. after 24 hours of incubation in the growth culture medium. In marked contrast, super hFGF1 showed negligible degradation (FIGS. 16A-16B). In 16B, the lanes are as follows: 1 & 5 immediately after addition of medium, 2 & 6—no medium, 3 & 7—medium with no cells for 24 hrs, 4 & 8—incubated with cells in medium for 24 hrs), So, according to the FIG. 16B, the wtFGF-1 band decreases in lane 4 when compared to lane 1 (which suggests that after 24 hours of incubation, the band intensity decreases, i.e., the wthFGF1 degrades in the culture medium. In contrast, super hFGF1, the band intensity remains almost unchanged suggesting that super hFGF1 is significantly more stable in the culture media than the wthFGF-1. The upper bands originate from the culture medium.

Cell signaling activity was measured by detecting the expression levels of phosphorylated ERK1/2 and Akt proteins. Super hFGF1 (SEQ ID NO: 2; S), as compared to wild type hFGF1 (SEQ ID NO: 1; WT), showed an increased activation of both these pathways especially, that of the ERK1/2 pathway which is known to be critical for the wound healing (FIG. 17).

Effect of wt hFGF1 and super hFGF1 activity on the cell migration was confirmed by the scratch assay. Coriell AG 21264 fibroblast cells exhibited an increased migration in presence of super hFGF1 compared to that of the wt-hFGF1 (FIG. 18).

Rate of wound closure was examined using C57Bl/6J mice to determine the effect(s) of healing caused by wt hFGF1 and super hFGF1. Percent rate closure of the dermal incision induced by super hFGF1 was higher as compared to that by wt-hFGF1 (FIG. 19). These results suggest that super hFGF1 exhibits higher wound healing properties which can be exploited towards the development of a potent and efficient wound healing formulation.

Example 2

An Engineered FGF2

Using the pairwise alignment and comparing the 3D structures of hFGF1 and hFGF2 (SEQ ID NO: 3). We have identified residues that are conserved in both these isoforms. Based on this information, residues in hFGF2 were mutated similar to that of superFGF1 for generating the super hFGF2 variant (SEQ ID NO: 4). Glutamine at $54^{th}$ position in hFGF1 was mutated to proline whereas in case of hFGF2, proline is already present in the same position. Hence, quadruple mutant Q65L N111S K128N K138E of FGF2 can be predicted to show enhanced stability and heparin independent bioactivity like super nFGF2.

Example 3

Comparison of Stability, Heparin Binding, and Cell Proliferation Activity of Mutations in Super FGF1

FGF1 mutants including various combinations of the amino acid substitutions found in super FGF1 were also characterized. A single FGF1 mutant included R123E-SM-FGF1 (SEQ ID NO: 1 with R123E single point mutation). Double FGF1 mutants included R123E/K113N-DM-FGF1 (SEQ ID NO: 1 with R123E and K113N mutations), R123E/H94S-DM-FGF1 (SEQ ID NO: 1 with R123E and H94S mutations), R123E/S48L-DM-FGF1 (SEQ ID NO: 1 with R123E and S48L mutations), and R123E/Q41P-DM-FGF1 (SEQ ID NO: 1 with R123E and Q41P mutations). Triple FGF1 mutants K113N/S48L-TM-FGF1 (SEQ ID NO: 1 with R123E, K113N and S48L mutations), K113N/H94S-TM-FGF1 (SEQ ID NO: 1 with R123E, K113N and H94S mutations), and K113N/Q41P-TM-FGF1 (SEQ ID NO: 1 with R123E, K113N and Q41P mutations).

Single Mutants

Figure 20:
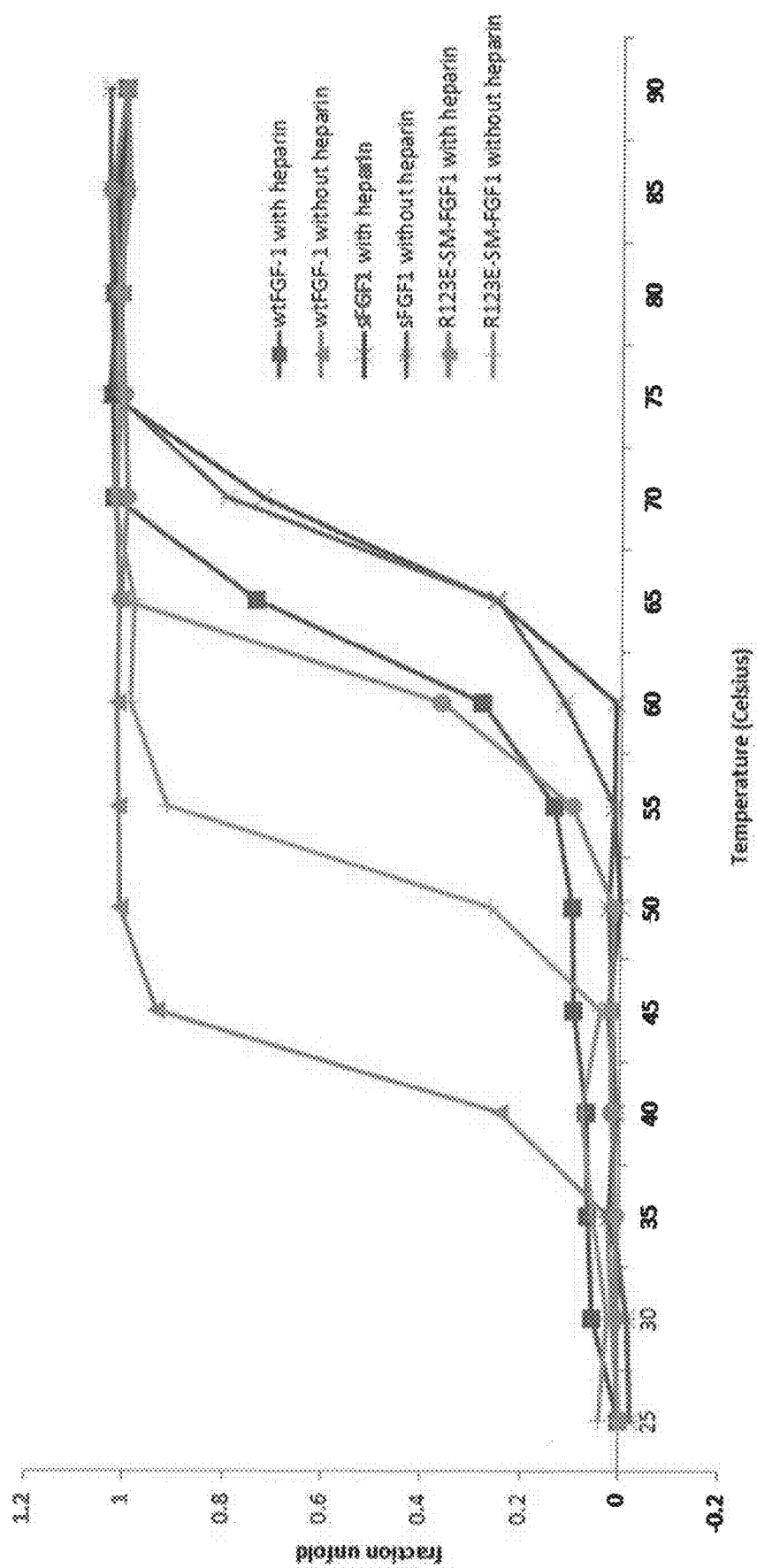
FIG. 20 shows a thermal stability analysis for wtFGF1, sFGF1, and R123E-SM-FGF1.

FIG. 20 indicates that super-FGF-1 is the most stable design of FGF-1. Unlike the other mutants tested in FIG. 20, the thermal stability of sFGF-1 stability is independent of heparin binding. The data in Table 1 suggests that the heparin-dependent thermal stability of sFGF-1 of the R123E mutation decreases as the heparin decreases (as compared to the wild type).

TABLE 1

Comparison of the thermal stability of SM-R123E as compared to wt-FGF1 and sFGF-1

| Protein | Without heparin (Celsius) | With heparin (Celsius) | Delta Tm (Celsius) |
|---|---|---|---|
| wtFGF1 | 42 | 63 | 21 |
| sFGF1 | 68 | 68 | 0 |
| R123E-SM-FGF1 | 52 | 61 | 9 |

Figure 21:
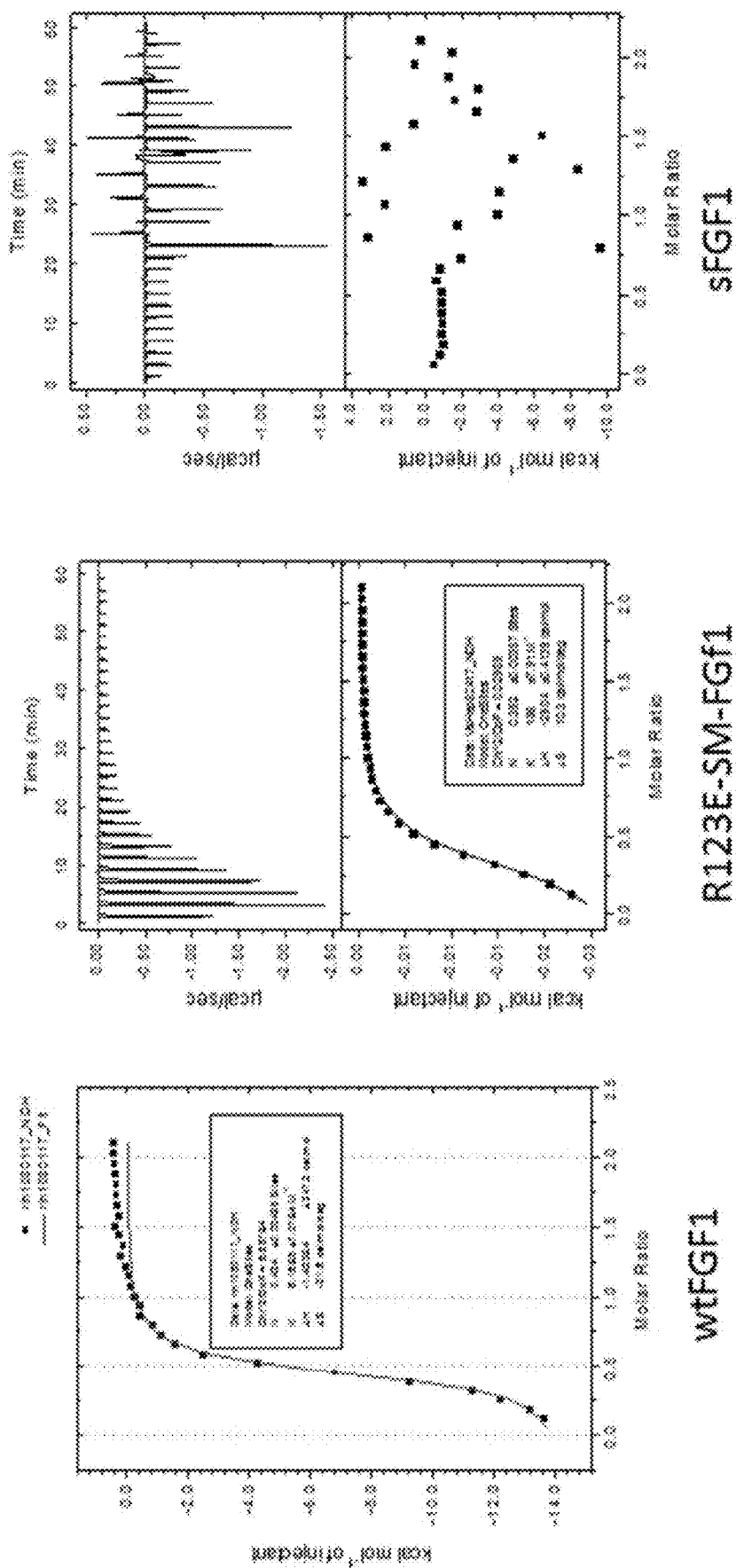
FIG. 21 shows the heparin binding affinity of R123E-SM-FGF mutant protein.

FIG. 21 shows that the heparin binding affinity ($K_d$=4.2 μM) of the R123E-SM-FGF1 mutant is lower than that of wtFGF-1 ($K_d$=1.6 μM). sFGF-1 (SEQ ID NO: 2) lacks heparin binding.

Figure 22:
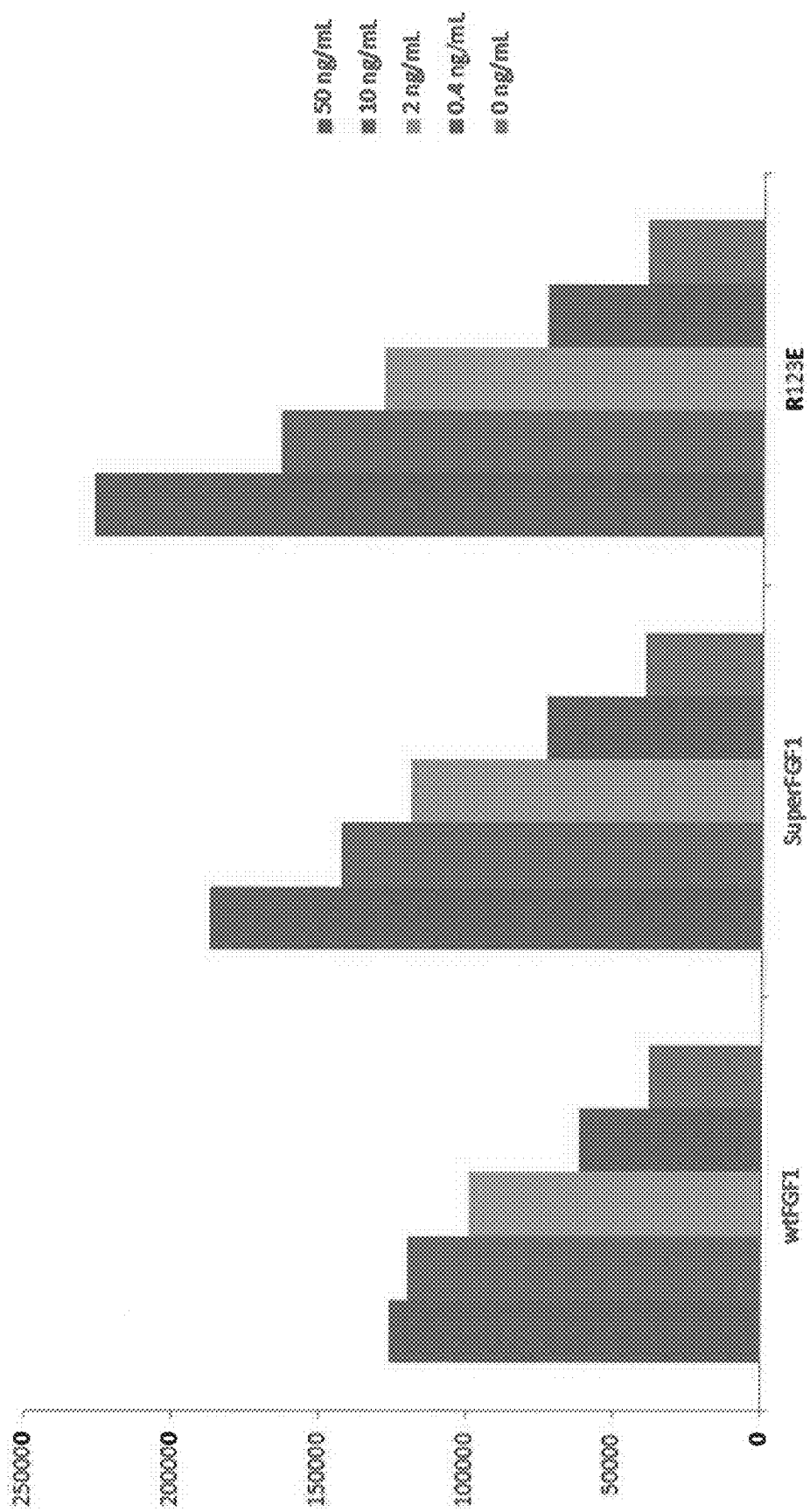
FIG. 22 shows the cell proliferation activity of wtFGF1, sFGF1, and R123E-SM-FGF1 proteins.

FIG. 22 shows that the R123E-SM-FGF1 mutation enhances the cell proliferation activity of the FGF1 protein as compared to the wt hFGF1. This mutation likely accounts for the enhanced cell proliferation activity of the super FGF1.

Double Mutants

Figure 23:
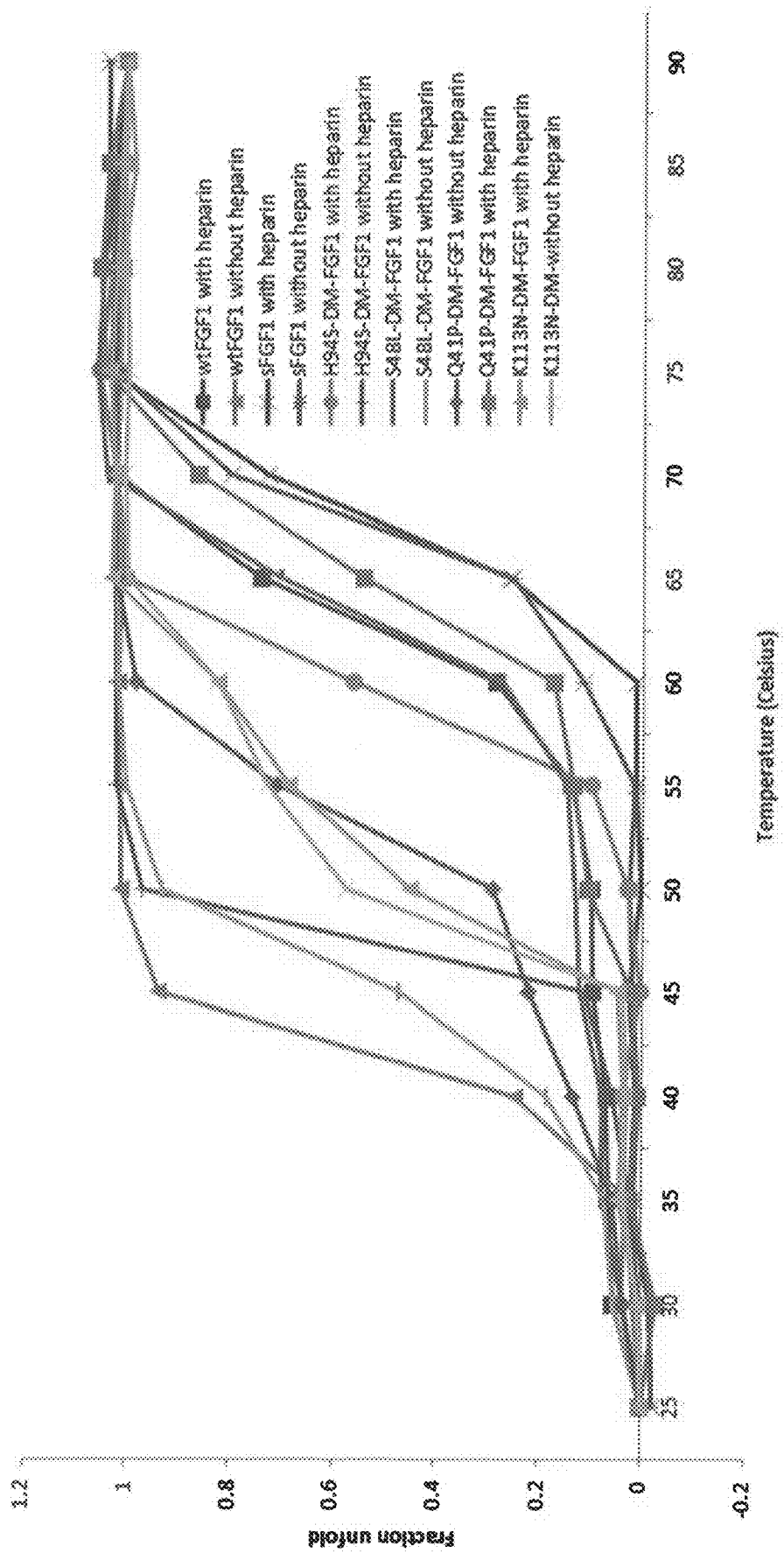
FIG. 23 shows a thermal stability analysis for wtFGF1, sFGF1, and double mutant (DM) FGF1 proteins.

As seen in FIG. 23, the thermal stability of the double mutant, K113N/R123E, is independent (like sFGF1) of heparin binding. The thermal stability of the other double mutants (DMs) [H94S/R123E, S48L/R123E, Q41P/R123E] increases in the presence of heparin.

The data in Table 2 indicates that sFGF1 is the most stable form. The thermal stability of sFGF1 and K113N-DM-FGF1 mutant is heparin independent.

TABLE 2

Thermal Stability of Double Mutant FGF1 proteins

| Protein | Without heparin (Celsius) | With heparin (Celsius) | Delta Tm (Celsius) |
|---|---|---|---|
| wtFGF1 | 42 | 63 | 21 |
| sFGF1 | 68 | 68 | 0 |
| K113N/R123E-DM-FGF1 | 49 | 50 | 1 |
| Q41P/R123E-DM-FGF1 | 52.5 | 62.5 | 10 |
| S48L/R123E-DM-FGF1 | 43 | 60 | 17 |
| H94S/R123E-DM-FGF1 | 46 | 58 | 12 |

Figure 24:
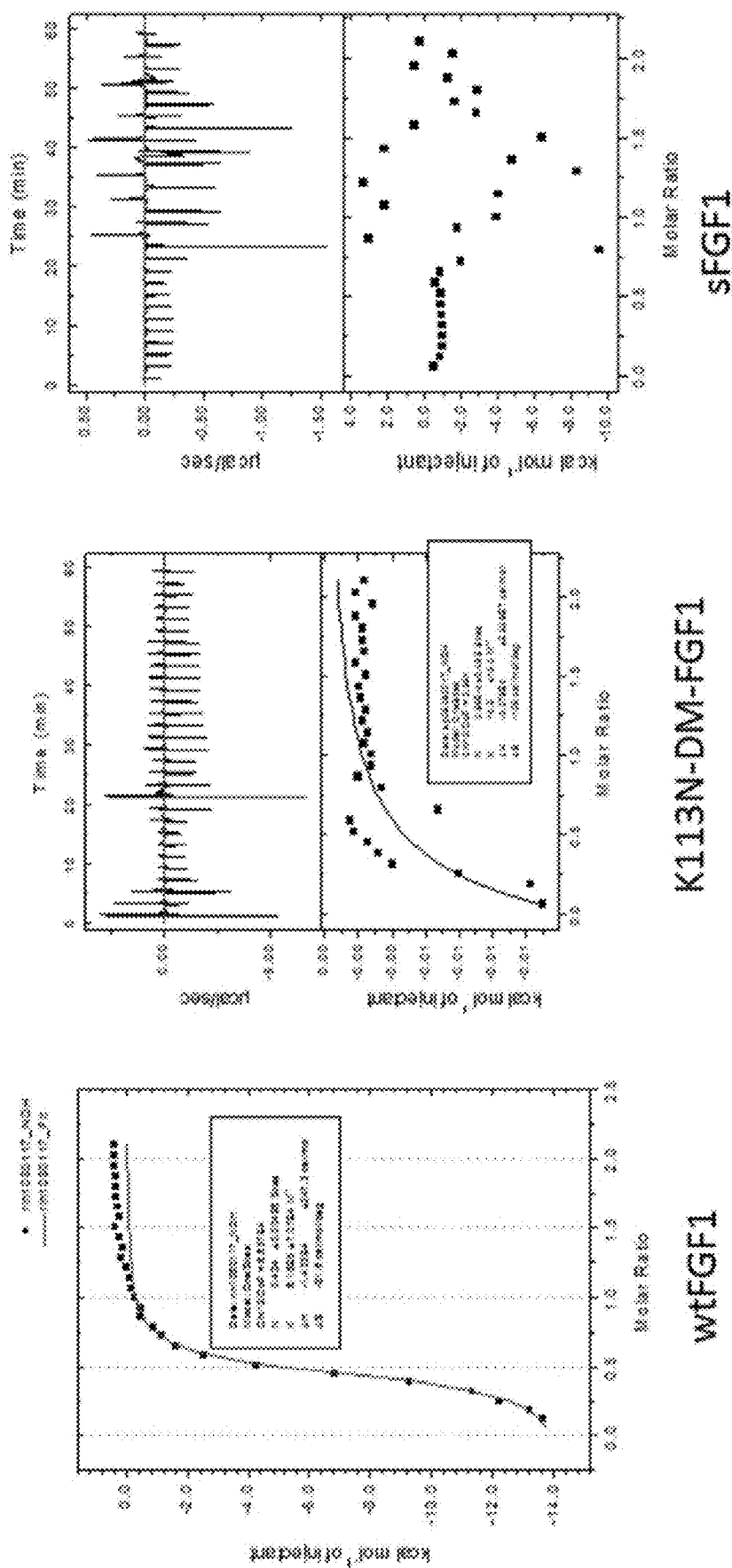
FIG. 24 shows the heparin binding affinity of double mutant FGF1 proteins.

The data in FIG. 24 shows that both sFGF1 and K113N/R123E-DM-FGF1 lack heparin binding. These results suggest that K113 and R123 are responsible for the heparin binding of FGF1.

Figure 25:
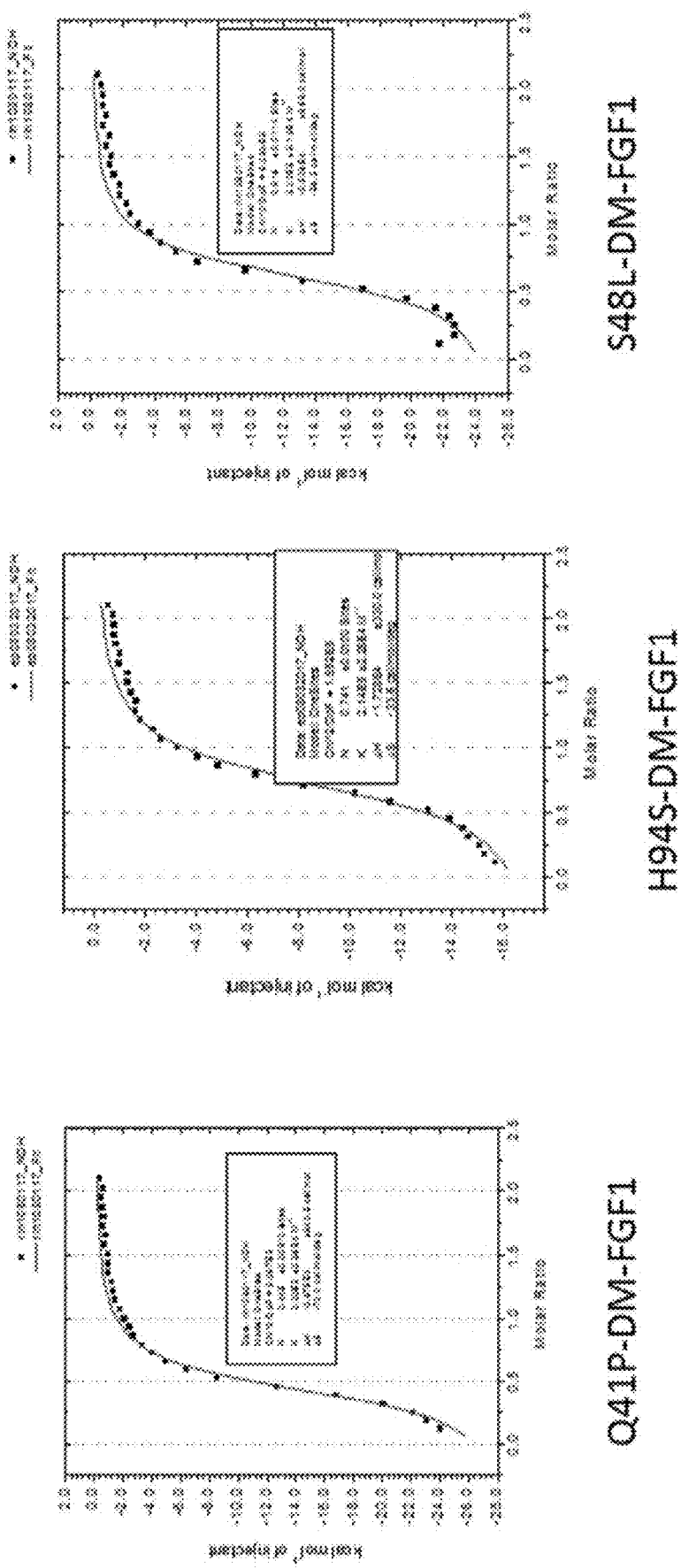
FIG. 25 shows the heparin binding affinity of double mutant FGF1 proteins.

FIG. 25 shows the heparin binding affinity of double mutants, S48L/R123E; H94S/R123E, and Q41P/R123E, is similar to the wild type FGF1.

Figure 26:
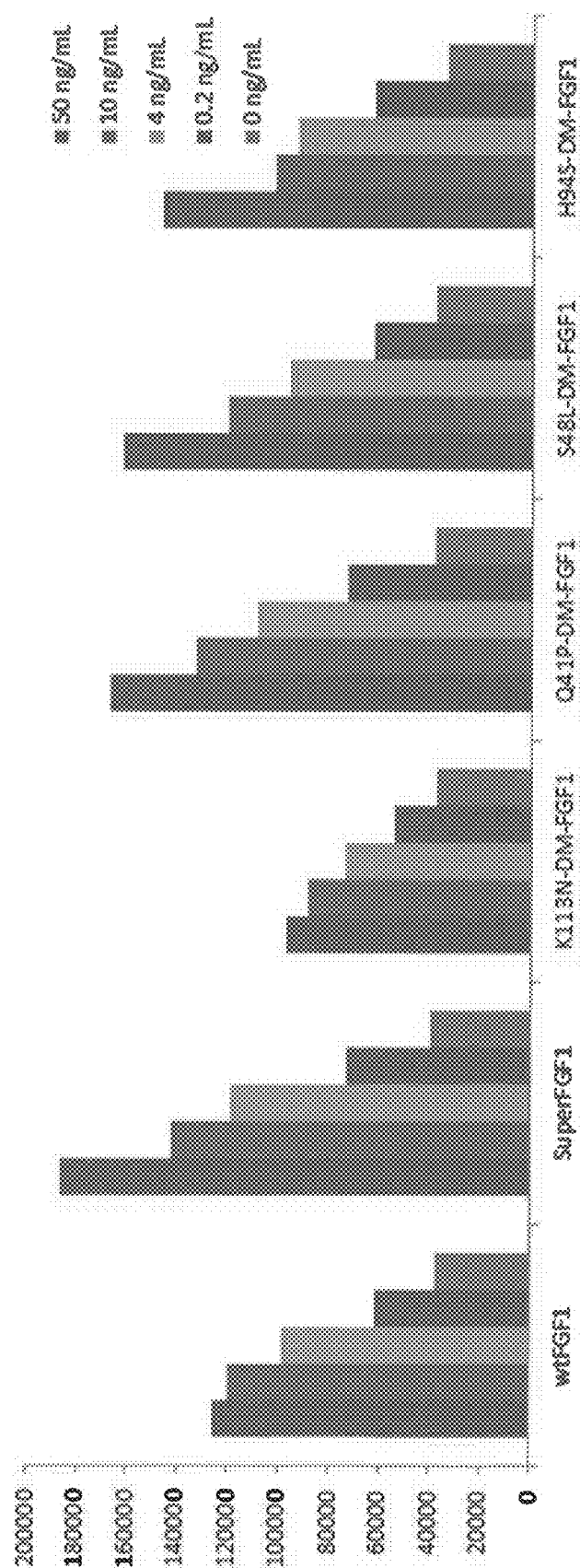
FIG. 26 shows the cell proliferation activity of wtFGF1, sFGF1, and double mutant FGF1 proteins.

The data in FIG. 26 shows that sFGF1 has highest bioactivity of all the proteins tested in FIG. 26.

Triple Mutants

Figure 27:
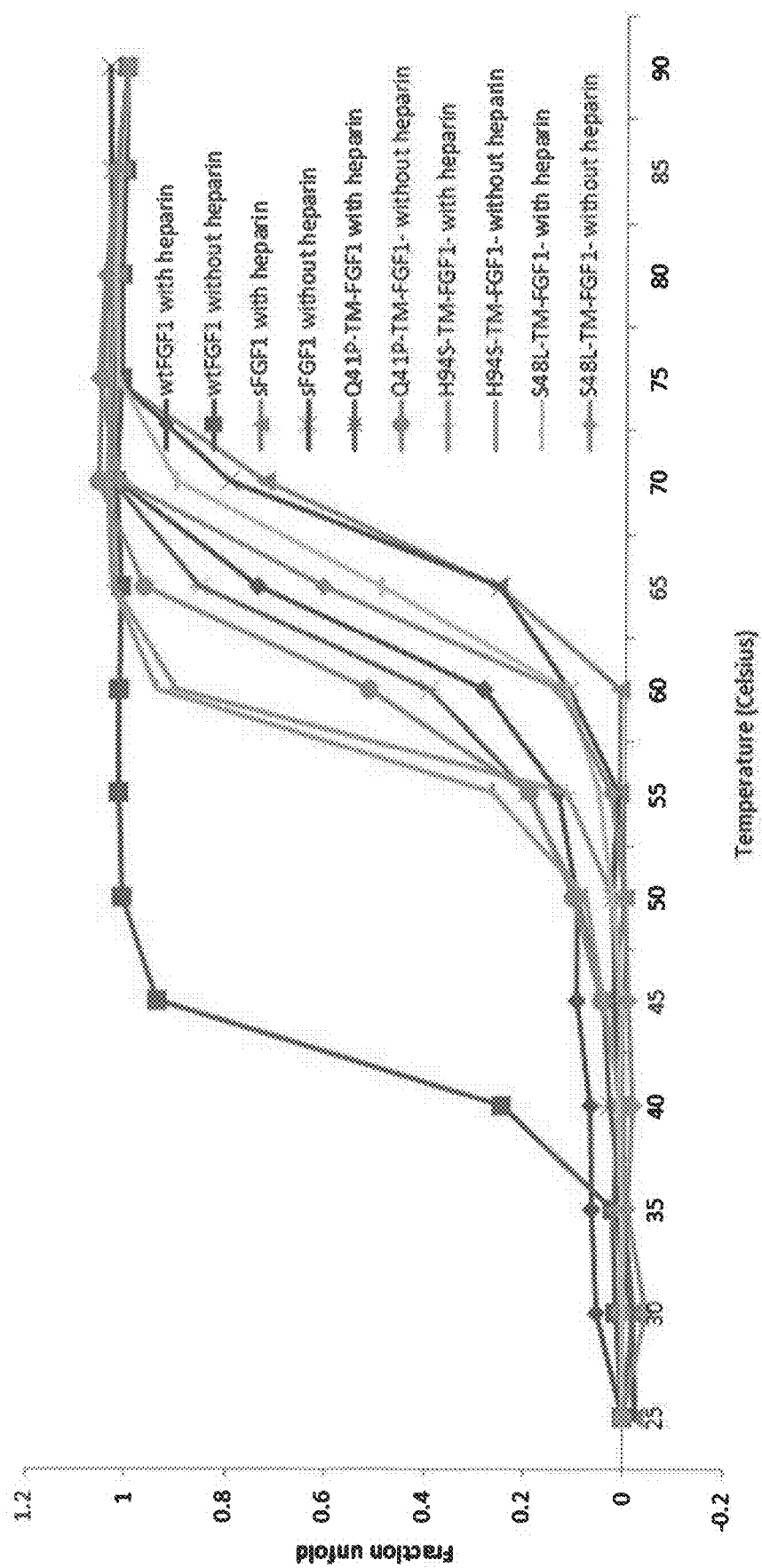
FIG. 27 shows a thermal stability analysis for wtFGF1, sFGF1, and triple mutant (TM) FGF1 proteins.

The data in FIG. 27 suggests that the thermal stability (in the presence and absence of heparin) of the designed triple mutants (Q41P/K113N/R123E; S48L/K113N/R123E; H94S/K113N/R123E) is similar to that of the double mutant, K113N/R123E.

The data in Table 3 suggests that the thermal stability (in the presence and absence of heparin) of the designed triple mutants (Q41P/K113N/R123E; S48L/K113N/R123E; H94S/K113N/R123E) is similar to that of the double mutant, K113N/R123E

TABLE 3

Thermal Stability of Triple Mutant FGF1 proteins

| Protein | Without heparin (Celsius) | With heparin (Celsius) | Delta Tm (Celsius) |
|---|---|---|---|
| wtFGF1 | 42 | 63 | 21 |
| sFGF1 | 68 | 68 | 0 |
| Q41P-TM-FGF1 | 58.5 | 0.5 | 1 |
| S48L-TM-FGF1 | 63 | 64 | 1 |
| H94S-TM-FGF1 | 55 | 56 | 1 |

Figure 28:
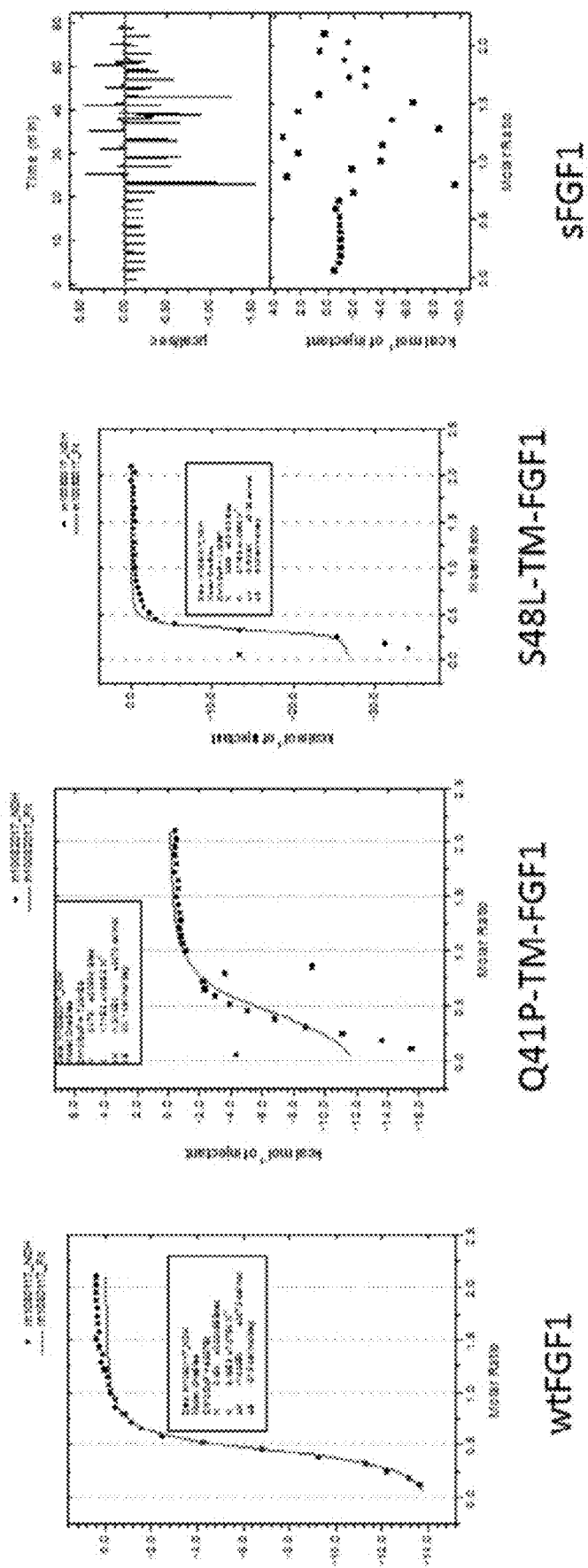
FIG. 28 shows the heparin binding affinity of triple mutant FGF1 proteins.

The data in FIG. 28 suggests that the heparin binding affinity of the designed triple mutants (Q41P/K113N/R123E; S48L/K1N/R123E) is similar to that of the double mutant, K113N/R123E.

Figure 29:
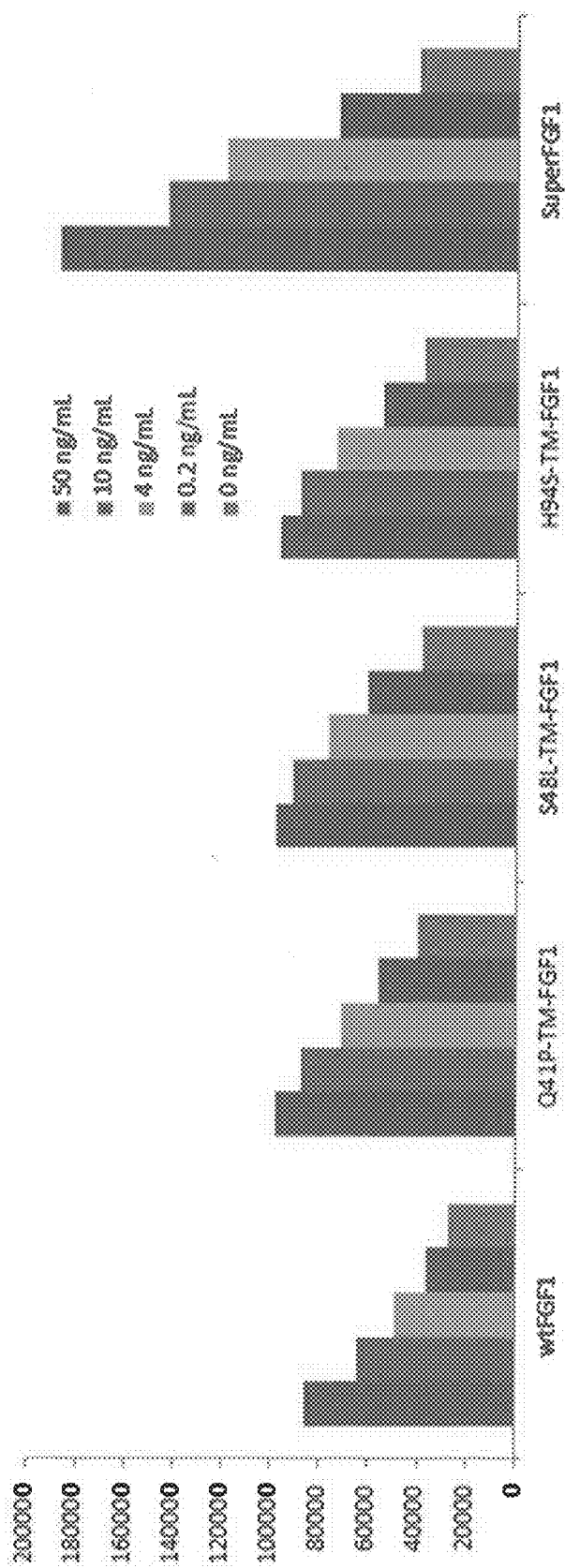
FIG. 29 shows the cell proliferation activity of wtFGF1, sFGF1, and triple mutant FGF1 proteins.

The data in FIG. 29 suggests that the cell proliferation activity of the designed triple mutants is significantly lower than that of sFGF1.

Stability of superFGF1 in Alcohols

Figure 30A:
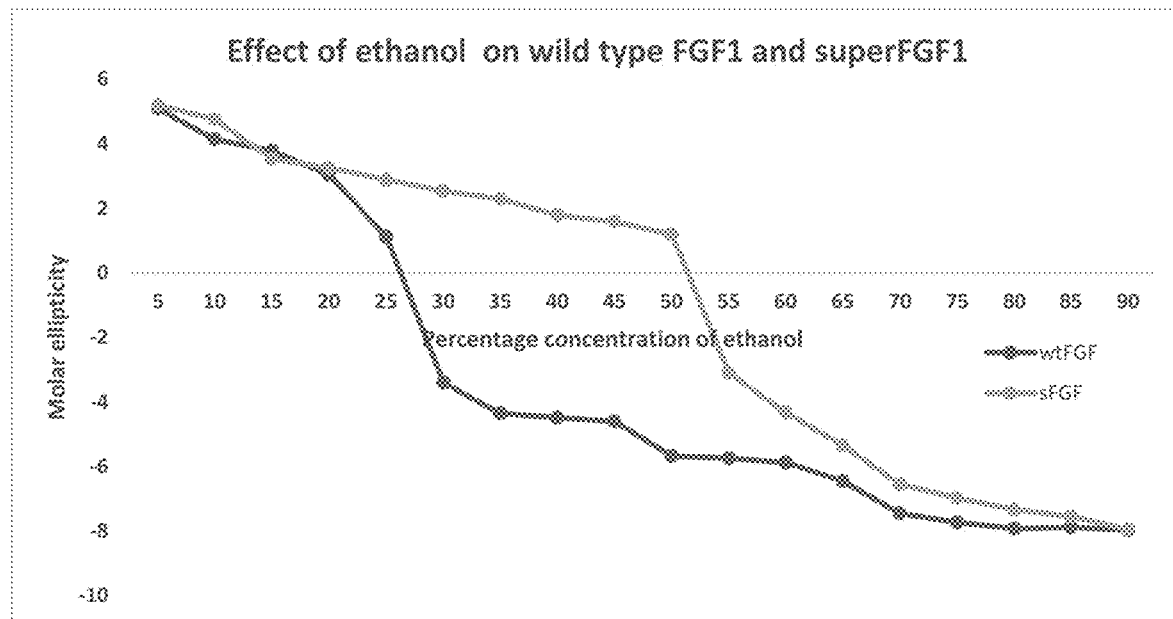
FIG. 30A is a graph showing the effect of ethanol on the stability of FGF1 and superFGF1 1 described herein at various concentrations of alcohol and demonstrates that the superFGF1 polypeptide is more stable in ethanol than the wild-type FGF1.
Figure 30B:
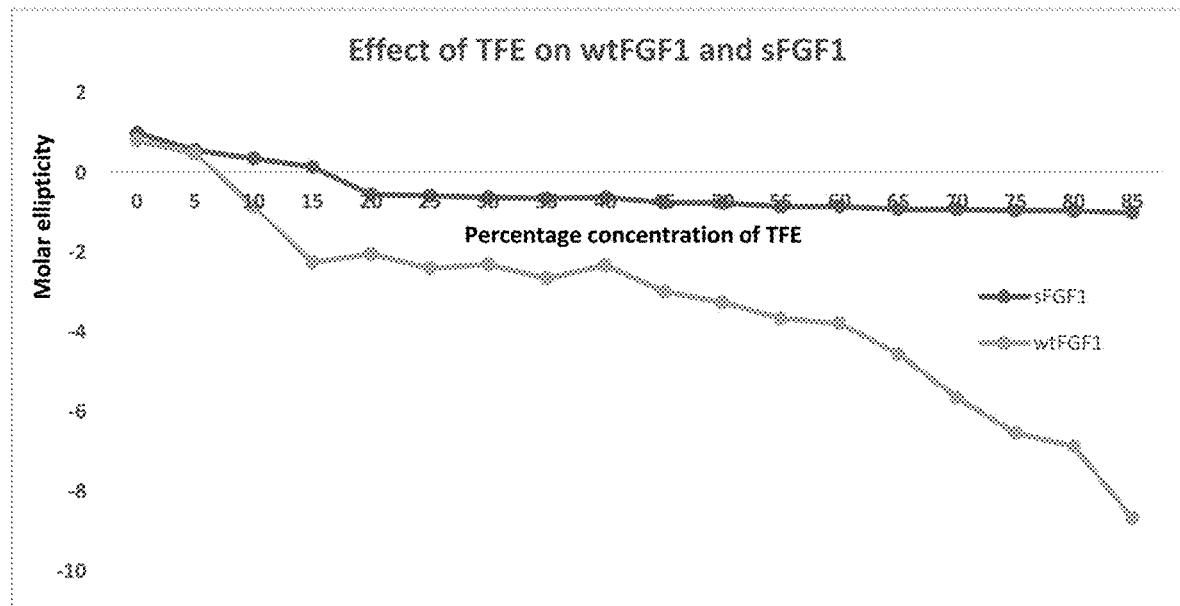
FIG. 30B is a graph showing the effect of 2,2,2, trifluoroethanol (TFE) on the stability of wild-type FGF1 as compared to superFGF1 at various concentrations of the TFE and demonstrates that the superFGF1 is more stable at higher concentrations of TFE.

Formulation of efficient FGF-based wound healing therapeutics requires the protein (FGF) to be stable to sterilizing and disinfecting agents such as, alcohols. In this context, we compared the effect(s) of two alcohols [ethanol and 2,2,2, trifluoroethanol (TFE)] on the stability of human wild type (SEQ ID NO: 1) and superFGF1 (SEQ ID NO: 2). The stability of the proteins was monitored by circular dichroism spectroscopy, a biophysical technique that provides information on the backbone folding (or secondary structure) of proteins. The results of these experiments clearly suggest that wildtype FGF1 is almost completely unfolded at around 30% v/v ethanol (FIG. 30A). However, in marked contrast, superFGF1 is stable and maintains its native backbone conformation even in ~50% v/v ethanol (FGF-1). Similarly, wild type FGF1 is found to denature at TFE concentrations greater than 5% v/v (FIG. 30B). Interestingly, on the other hand, the structure of superFGF1 appears to be almost unperturbed over a TFE concentration range of 0-90% v/v (FIG. 30B). The extraordinary stability of superFGF1 to alcohols implies that is can be stored under sterile conditions in alcohol(s). Consequently, potential infections during FGF-mediated wound healing process(es) can be significantly minimized.

We claim:

1. A FGF1 polypeptide comprising at least 90% sequence identity to SEQ ID NO: 1 and comprising amino acid substitutions at least at residues Q41, S48, H94, K113, and R123 of SEQ ID NO: 1, or a functional fragment of the FGF1 polypeptide thereof
   wherein the substitution at residue Q41 is selected from the group consisting of Q41P, Q41F, Q41M, Q41Y, Q41W, Q41I, Q41L, Q41V, and Q41A;
   wherein the substitution at residue S48 is selected from the group consisting of S48L, S48A, S48V, S48P, S48T, S48M, S48I, S48F, S48Y, and S48W;
   wherein the substitution at residue H94 is selected from the group consisting of H94S, H94T, H94K, H94R, and H94Y;
   wherein the substitution at residue K113 is selected from the group consisting of K113N, K113Q, K113S, K113T, K113R, and K113Y;
   and wherein the substitution at residue R123 is selected from the group consisting of R123E and R123D.

2. The FGF1 polypeptide of claim 1, wherein the FGF1 polypeptide comprises the substitutions Q41P, S48L, H94S, K113N, and R123E.

3. The FGF1 polypeptide of claim 1, wherein the FGF1 polypeptide comprises SEQ ID NO: 2.

4. A fusion protein comprising the FGF1 polypeptide of claim 1 and a membrane permeable peptide.

5. A pharmaceutical composition comprising the FGF1 polypeptide of claim 1 and a pharmaceutical carrier.

6. A hydrogel comprising the FGF1 polypeptide of claim 1.

7. A method of promoting wound healing in a subject in need thereof comprising administering a therapeutically effective amount of the FGF1 polypeptide of claim 1 to the subject.

8. The method of claim 7, wherein the subject is a mammal.

* * * * *

```
                           SEQUENCE LISTING

<160> NUMBER OF SEQ ID NOS: 4

<210> SEQ ID NO 1
<211> LENGTH: 141
<212> TYPE: PRT
<213> ORGANISM: Artificial Sequence
<220> FEATURE:
<223> OTHER INFORMATION: Synthetic: wtFGF1

<400> SEQUENCE: 1

Met Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 2
<211> LENGTH: 141
<212> TYPE: PRT
<213> ORGANISM: Artificial Sequence
<220> FEATURE:
<223> OTHER INFORMATION: Synthetic: shFGF1

<400> SEQUENCE: 2

Met Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Pro His Ile Gln Leu Gln Leu Leu
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn Ser Tyr Asn
                85                  90                  95

Thr Tyr Ile Ser Lys Lys His Ala Glu Lys Asn Trp Phe Val Gly Leu
            100                 105                 110

Asn Lys Asn Gly Ser Cys Lys Arg Gly Pro Glu Thr His Tyr Gly Gln
```

```
                115                 120                 125
Lys Ala Ile Leu Phe Leu Pro Leu Pro Val Ser Ser Asp
    130                 135                 140

<210> SEQ ID NO 3
<211> LENGTH: 155
<212> TYPE: PRT
<213> ORGANISM: Artificial Sequence
<220> FEATURE:
<223> OTHER INFORMATION: Synthetic: wtFGF2

<400> SEQUENCE: 3

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 4
<211> LENGTH: 155
<212> TYPE: PRT
<213> ORGANISM: Artificial Sequence
<220> FEATURE:
<223> OTHER INFORMATION: Synthetic: shFGF2

<400> SEQUENCE: 4

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Leu Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Ser Tyr
            100                 105                 110

Asn Thr Tyr Arg Ser Arg Lys Tyr Thr Ser Trp Tyr Val Ala Leu Asn
        115                 120                 125
```

```
-continued

Arg Thr Gly Gln Tyr Lys Leu Gly Ser Glu Thr Gly Pro Gly Gln Lys
    130                 135                 140

Ala Ile Leu Phe Leu Pro Met Ser Ala Lys Ser
145                 150                 155
```